US012661056B2

(12) United States Patent
Searson et al.

(10) Patent No.: US 12,661,056 B2
(45) Date of Patent: Jun. 23, 2026

(54) CAPACITIVE SWEAT RATE SENSOR

(71) Applicant: THE JOHNS HOPKINS UNIVERSITY, Baltimore, MD (US)

(72) Inventors: Peter Charles Searson, Baltimore, MD (US); Dong-Hoon Choi, Baltimore, MD (US); Dinh-Tuan Phan, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 785 days.

(21) Appl. No.: 17/997,574

(22) PCT Filed: Jul. 27, 2021

(86) PCT No.: PCT/US2021/070991
§ 371 (c)(1),
(2) Date: Oct. 31, 2022

(87) PCT Pub. No.: WO2022/027019
PCT Pub. Date: Feb. 3, 2022

(65) Prior Publication Data
US 2023/0210447 A1 Jul. 6, 2023

Related U.S. Application Data

(60) Provisional application No. 63/057,651, filed on Jul. 28, 2020.

(51) Int. Cl.
A61B 5/00 (2006.01)
(52) U.S. Cl.
CPC ............ A61B 5/4266 (2013.01); A61B 5/681 (2013.01); A61B 5/6833 (2013.01)

(58) Field of Classification Search
CPC . A61B 5/14517; A61B 5/4266; A61B 5/6833; A61B 5/1477; A61B 5/053;
(Continued)

(56) References Cited

U.S. PATENT DOCUMENTS 9,955,908 B2 5/2018 Revol-Cavalier et al.
2010/0305420 A1* 12/2010 Curry ................. G01N 27/3272
257/E29.166
(Continued)

FOREIGN PATENT DOCUMENTS

EP 0421625 A1 4/1991
GB 2452258 A 3/2009
(Continued)

OTHER PUBLICATIONS

Doherty, F. (Authorized officer), International Preliminary Report on Patentability issued in corresponding International Application No. PCT/US2021/070991 mailed on Feb. 9, 2023, 7 pages.
(Continued)

*Primary Examiner* — Patrick Fernandes
*Assistant Examiner* — Shawn Curtis Broughton
(74) *Attorney, Agent, or Firm* — MH2 Technology Law Group LLP

(57) ABSTRACT

A sweat sensor includes a first conductor and a second conductor that are parallel with one another. The sweat sensor also includes a channel disposed between the first and second conductors. The channel is configured to receive a sample of sweat. A measure of capacitance between the first and second conductors changes based at least partially upon a volume of the sweat in the channel.

20 Claims, 28 Drawing Sheets

(58) Field of Classification Search
CPC ... A61B 5/0531; A61B 5/0537; A61B 5/7275;
A61B 5/7246; A61B 10/0064; A61B
2562/164
See application file for complete search history.

(56) References Cited

U.S. PATENT DOCUMENTS

| | | |
|---|---|---|
| 2018/0064377 A1 | 3/2018 | Rogers et al. |
| 2019/0117170 A1 | 4/2019 | Begtrup et al. |
| 2020/0107558 A1* | 4/2020 | Lenigk .................... A23G 9/28 |
| 2020/0107758 A1 | 4/2020 | Lenigk et al. |

FOREIGN PATENT DOCUMENTS

| | | |
|---|---|---|
| KR | 101465016 B1 | 10/2014 |
| SU | 1134183 A1 | 1/1985 |
| SU | 1512564 A1 | 10/1989 |
| WO | 2017058806 A1 | 4/2017 |
| WO | 2018223058 A1 | 12/2018 |
| WO | WO-2018223090 A1 * | 12/2018 ........ A61B 5/14517 |
| WO | 2019023195 A1 | 1/2019 |
| WO | 2019104118 A1 | 5/2019 |
| WO | 2019126188 A9 | 6/2019 |
| WO | 2019183529 A1 | 9/2019 |

OTHER PUBLICATIONS

Makarova, O. (Authorized officer), International Search Report and Written Opinion in corresponding International Application No. PCT/US2021/070991 mailed on Sep. 23, 2021, 8 pages.
Hinin Yin Yin Nyein et al, "A Wearable Microfluidic Sensing Patch for Dynamic Sweat Secretion Analysis". ACS Sens., 2018, 3, 5, 944-952.

* cited by examiner

LCR METER

DUT

CONSTANT
FLOW

SYRINGE PUMP

TOP PDMS MICROCHANNEL LAYER

MIDDLE PDMS SEALING LAYER

BOTTOM DOUBLE-SIDED ADHESIVE LAYER

SWEAT INLET

SWEAT INLET

PDMS

LIQUID METAL ELECTRODES

SWEAT OUTLET

LIQUID METAL ELECTRODES

OUTLET

INSULATING LAYER

TOP CONTDUCTING PLATE
(ITO) PET SUBSTRATE

MICROFLUIDIC LAYER
(DOUBLE-SIDED ADHESIVE TAPE)

ENGRAVED LINE

PET SUBSTRATE BOTTOM
CONDUCTING PLATE (ITO)

INLET

INSULATING LAYER

SKIN-DEVICE INTERFACE
LAYER (DOUBLE-SIDED
ADHESIVE TAPE)

WEARABLE SWEAT
RATE SENSOR

PLASTIC SUBSTRATE
TOP CONDUCTING PLATE
INSULTING LAYER

2ND MICROFLUIDIC LAYER

INSULTING LAYER
MIDDLE TOP CONDUCTING PLATE
PLASTIC SUBSTRATE
MIDDLE BOTTOM CONDUCTING PLATE
INSULTING LAYER

1ST MICROFLUIDIC LAYER

INSULTING LAYER
TOP CONDUCTING PLATE
FLEXIBLE PLASTIC SUBSTRATE

SKIN-DEVICE INTERFACE LAYER

CAPACITIVE SWEAT RATE SENSOR

CROSS-REFERENCE TO RELATED APPLICATIONS

This patent application is the national stage entry of International Patent Application No. PCT/US2021/070991, filed on Jul. 27, 2021, and published as WO 2022/027019 A1 on Feb. 3, 2022, which claims the benefit of U.S. Provisional Patent Application No. 63/057,651, filed on Jul. 28, 2020, both of which are hereby incorporated by reference herein in their entireties.

FIELD OF THE DISCLOSURE

The present disclosure relates generally to sensors. More particularly, the present disclosure relates to a capacitive-type sweat rate sensor.

BACKGROUND OF THE DISCLOSURE

Sweating is the most effective thermal regulation method for humans, but excessive water and electrolyte loss contribute to heat-related illnesses, such as hypo- and hyper-natremia. It is well known that water losses of greater than 2% of the body weight decrease human performance. Water and electrolyte loss are linked to muscle weakness, fatigue, and cramps. Furthermore, working in hot environments with poor hydration has been linked to chronic kidney diseases.

It would therefore be advantageous to provide a capacitive sweat rate sensor that tracks sweat rate in real time with an easy to manufacture design.

SUMMARY

In accordance with an aspect of the present disclosure, a device includes a pair of parallel plates including a first and second parallel plate. The device includes a microfluidic channel disposed between the pair of parallel plates. The microfluidic channel is configured to receive a sample of sweat. A measure of capacitance between the first parallel plate and the second parallel plate changes depending on a volume of the sweat in the microfluidic channel.

In accordance with an aspect of the present disclosure, the pair of parallel plates includes layers. The layers include a top insulating layer, a top parallel plate formed on a top substrate, a supporting layer, a bottom parallel plate formed on a bottom substrate, and a bottom insulating layer. The supporting layer is interposed between the top and bottom substrate, and these three layers form the microfluidic channel to collect the sweat sample during perspiration. The top and bottom parallel plates are formed on the opposite sides of the substrate which do not face the supporting layer. The top and bottom parallel plates are covered by the top and bottom insulating layers, respectively.

In accordance with another aspect of the present disclosure, a device includes a pair of parallel metal lines. Each line of the pair of parallel metal lines includes an electrode line. A microfluidic channel is disposed between the electrode lines. The microfluidic channel is configured to receive a sample of sweat. A measure of capacitance between the electrode lines changes depending on a volume of the sweat in the microfluidics channel.

In accordance with still another aspect of the present disclosure, the device includes two insulating substrates. The microfluidic channel and the two electrode lines are interposed between the two insulating substrates. The microfluidic channel is interposed between the two electrode lines, and the electrode lines and the microfluidic channel are horizontally overlapped.

In accordance with yet another aspect of the present disclosure, a device includes an insulating plate. A microfluidic channel is disposed in an interior space defined by the insulating plate. The microfluidic channel is configured to receive a sample of sweat. A pair of conductors is included. The conductors are also disposed within the interior space defined by the insulating plate. The microfluidic channel is interposed between the conductors, such that a capacitance between the two conductors changes depending on a volume of the sweat in the microfluidic channel.

In accordance with another aspect of the present disclosure, the microfluidic channel is configured to hold a predetermined amount of sweat. The conductors and the microfluidic channel are horizontally overlapped. The device includes multiple layers of insulators, microfluidic channels, and conductors. The conductors take the form of one selected from a group consisting of a conductive plate and a conductive line.

In accordance with yet another aspect of the present disclosure, the sweat sensor includes a first conductor and a second conductor that are parallel with one another. The sweat sensor also includes a channel disposed between the first and second conductors. The channel is configured to receive a sample of sweat. A measure of capacitance between the first and second conductors changes based at least partially upon a volume of the sweat in the channel.

In accordance with yet another aspect of the present disclosure, the sweat sensor includes a bottom insulating layer defining an inlet that is configured to receive sweat. The sweat sensor also includes a bottom plate positioned above the bottom insulating layer. The sweat sensor also includes a supporting layer positioned above the bottom plate. The supporting layer defines a channel that is in fluid communication with the inlet. The sweat sensor also includes a top plate positioned above the supporting layer. The bottom plate and the top plate include a conductive material. The bottom plate and the top plate are parallel with one another. The sweat sensor also includes a top insulating layer defining an outlet that is in fluid communication with the channel. The bottom insulating layer and the top insulating layer include a non-conductive material. The sweat sensor also includes a first electrode positioned at least partially within the supporting layer. The first electrode is electrically-connected to the bottom plate. The first electrode is electrically-isolated from the top plate. The sweat sensor also includes a circuit configured to measure a capacitance between the bottom plate and the top plate, and determine a rate of the sweat based at least partially upon the capacitance.

In accordance with yet another aspect of the present disclosure, the sweat sensor includes a bottom insulating layer configured to be placed in contact with a user's skin. The bottom insulating layer defines an inlet that is configured to receive sweat from the user's skin. The sweat sensor also includes a bottom plate positioned above the bottom insulating layer. The sweat sensor also includes a supporting layer positioned above the bottom plate. The supporting layer defines a channel that is configured to receive the sweat from the inlet. The sweat sensor also includes a top plate positioned above the supporting layer. The bottom plate and the top plate include a conductive material. The bottom plate and the top plate are parallel with one another. The sweat sensor also includes a top insulating layer defining an outlet that is configured to receive the sweat from the channel. The bottom insulating layer and the top insulating layer include a non-conductive material. The sweat sensor also includes a first electrode positioned at least partially within the supporting layer. The first electrode is electrically-connected to one of the bottom plate and the top plate. The first electrode is electrically-isolated from the other of the bottom plate and the top plate. The sweat sensor also includes a second electrode positioned at least partially within the supporting layer. The sweat sensor also includes a third electrode positioned at least partially within the supporting layer. The second and third electrodes are positioned on opposite sides of the channel and configured to be contacted by the sweat in the channel. The sweat sensor also includes a circuit configured to measure a capacitance between the bottom plate and the top plate, and determine a rate of the sweat based at least partially upon the capacitance. The circuit is also configured to measure an impedance between the second and third electrodes, and determine a conductivity of the sweat based at least partially upon the impedance.

BRIEF DESCRIPTION OF THE FIGURES

FIG. 15C illustrates a bottom and FIG. 15D illustrates a top view of the sweat conductivity sensor. To measure the conductivity of the sweat sample newly collected in the microfluidic channel, the sensor may be placed near the inlet of the microfluidic channel and the distance (d) between conductivity electrodes should be short.

DETAILED DESCRIPTION OF THE PREFERRED EMBODIMENTS

Figure 1A:
FIGS. 1A and 1B illustrate sectional and exploded views of a sweat rate sensor, according to a "parallel plate" embodiment of the present disclosure.
Figure 1A:
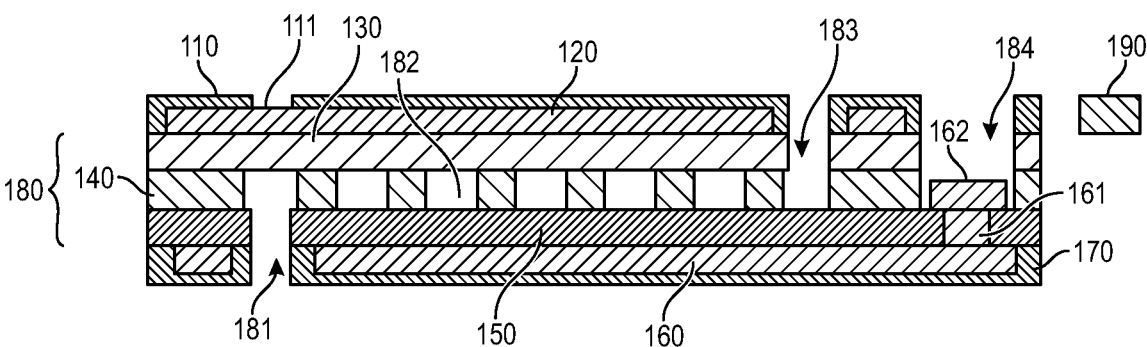

The presently disclosed subject matter now will be described more fully hereinafter with reference to the accompanying Drawings, in which some, but not all embodiments of the disclosures are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims.

In contrast to conventional sweat rate sensors, the wearable capacitive sweat rate sensors in the present disclosure monitor sweat rate continuously and in real time during measurement. In one embodiment, the capacitive-type sweat rate sensors described in this disclosure include a simple, unique structure with only one electrode pair. The fabrication process for the capacitive-type sweat rate sensor of the present disclosure is also very simple and mass-producible.

There are multiple embodiments possible to achieve a capacitive-type sweat rate sensor, according to an embodiment of the present disclosure. These include, but are not limited to, a sweat rate sensor with two parallel plates ("parallel plate" embodiment) and a sweat rate sensor having two parallel metal lines ("liquid metal" embodiment).

The sweat rate sensor with two parallel plates includes a top insulating layer, a top parallel plate formed on a top substrate, a supporting layer and a bottom parallel plate formed on a bottom substrate, and a bottom insulating layer. The supporting layer is interposed between the top and bottom substrates, and these three layers form a microfluidic channel to collect the sweat sample during perspiration. The top and bottom parallel plates are formed on the opposite sides of the substrate which do not face the supporting layer. The top and bottom parallel plates are covered by the top and bottom insulating layers, respectively. The capacitance between the two plates may change depending on the volume of the sweat sample in the microfluidic channel.

The "liquid metal" embodiment of the sweat rate sensor includes two electrode lines, two insulating layers, and a microfluidic channel. The microfluidic channel and two electrode lines are interposed between the two insulating layers. The microfluidic channel is interposed between the two electrode lines, and the electrode lines and the microfluidic channel are horizontally overlapped. The capacitance between the two electrode lines may change depending on the volume of the sweat sample in the fluidic channel.

Figure 1B:
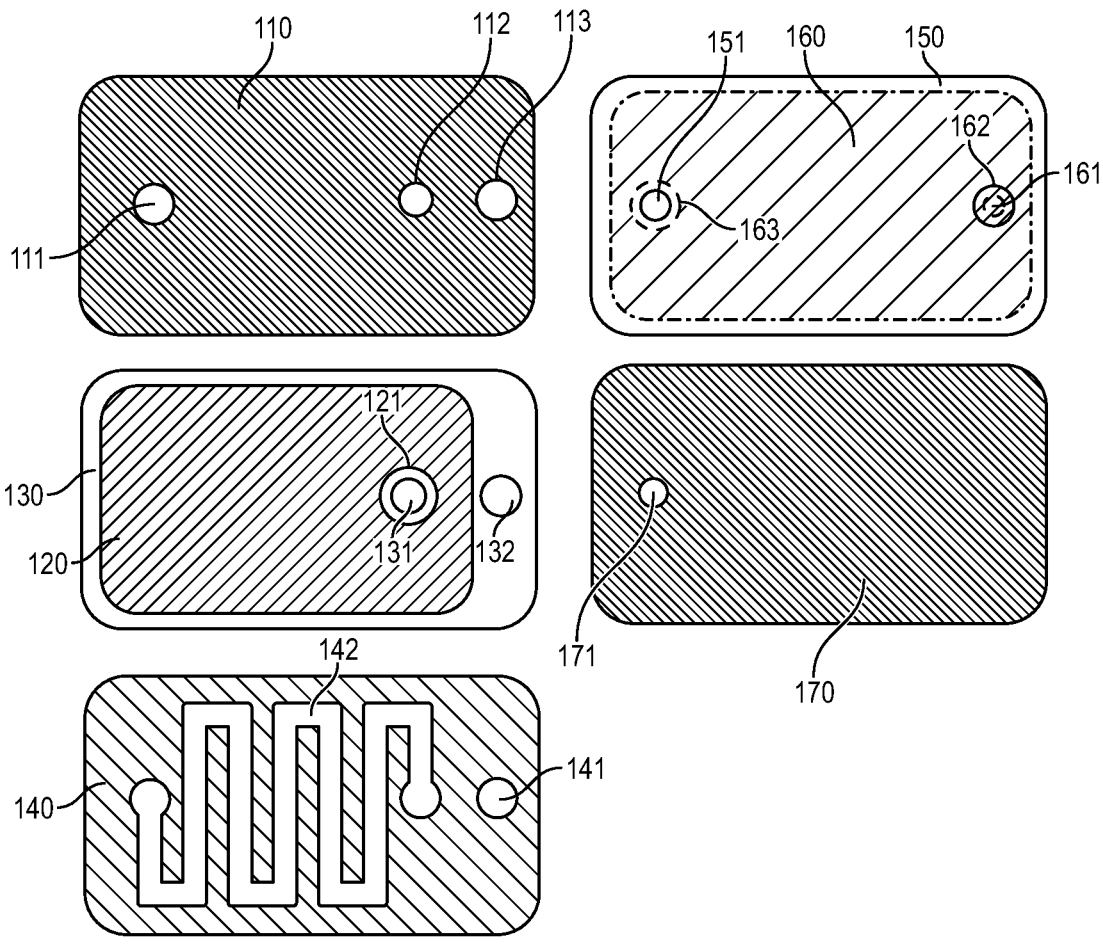

FIGS. 1A and 1B illustrate sectional and exploded views of a sweat rate sensor, according to a "parallel plate" embodiment of the present disclosure. The sweat rate sensor 100 with two parallel plates includes five layers: a top insulating layer 110, a top parallel plate 120 formed on a top substrate 130, a supporting layer 140, a bottom parallel plate 160 formed on a bottom substrate 150, and a bottom insulating layer 170. Further, as illustrated in FIGS. 1A and 1B the bottom substrate 150 may have a via 161 and an extended electrode 162. The bottom parallel plate 160, the via 161, and the extended electrode 162 are electrically connected. The top substrate 130, the bottom substrate 150, and the supporting layer 140 form a sweat collector 180. The sweat collector 180 has an inlet 181, a microfluidic channel 182, and an outlet 183, and collects a sweat sample on the skin during perspiration. The top insulating layer 110 has openings 111, 112, 113 for the top parallel plate 120, the outlet 183, and the extended electrode 162.

The top parallel plate 120 has an opening 121 for outlet 183, and the top substrate 130 has openings 131, 132 for outlet 183 and the extended electrode 162. The opening 131 is smaller than the opening 121. The supporting layer 140 has a (e.g., winding and/or serpentine) pattern 142 for the inlet 181, the outlet 183, and the microfluidic channel 182. The supporting layer also has an opening 141 for the extended electrode 162. The bottom substrate 150 has an opening 151 for the inlet 181. The bottom parallel plate 160 has an opening 163 for the inlet 181. The bottom insulating layer 170 has an opening 171 for the inlet 181. The opening 163 is larger than the opening 151 and 171. The top insulating layer 110, the top substrate 130, the bottom substrate 150, and the bottom insulating layer 170 may be a non-conductive material. The top and bottom parallel plate may be a conductive material.

Figure 2A:
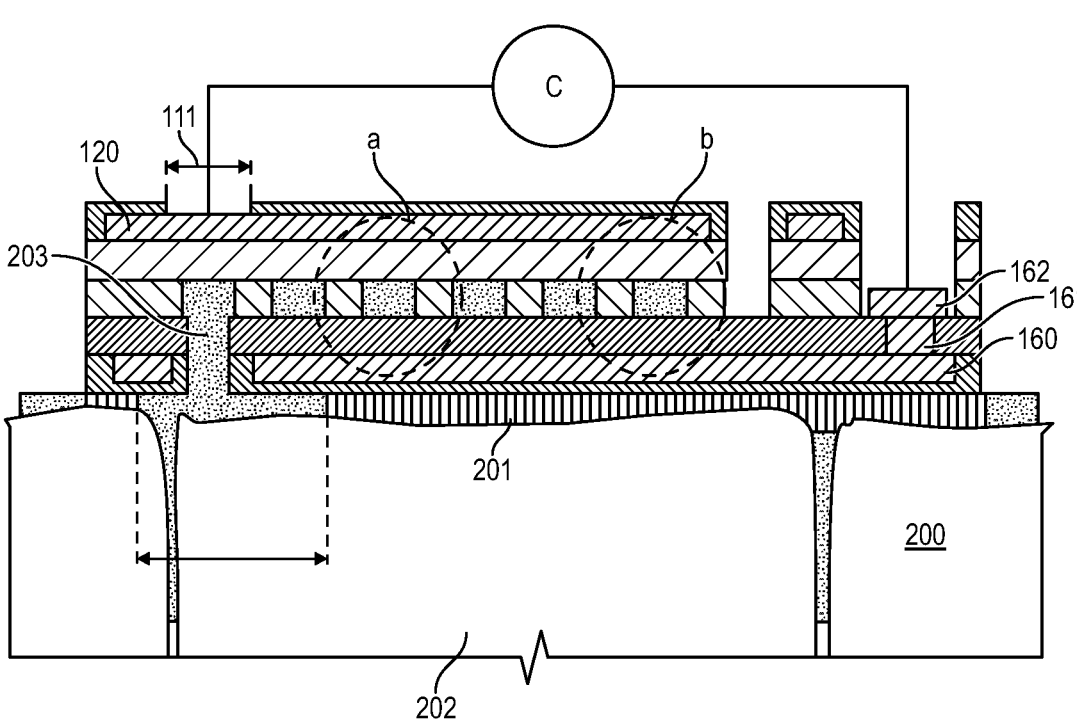
FIGS. 2A and 2B illustrate sectional and top-down views of a sensor according to a "parallel plate" embodiment of the present disclosure during sample collection.
Figure 2B:
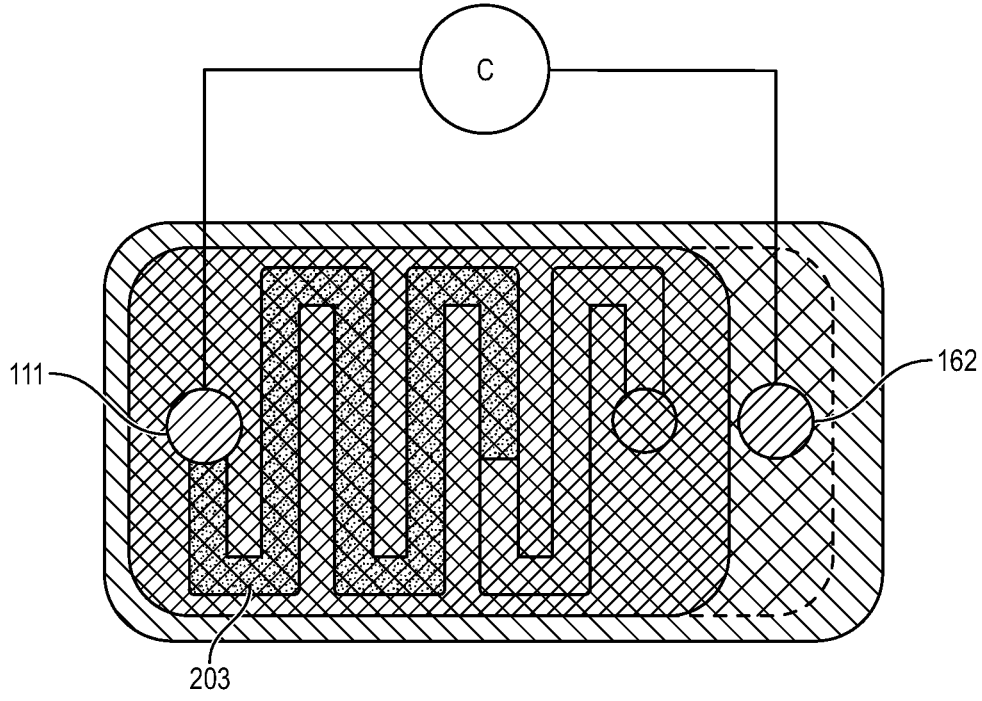
Figure 2C:
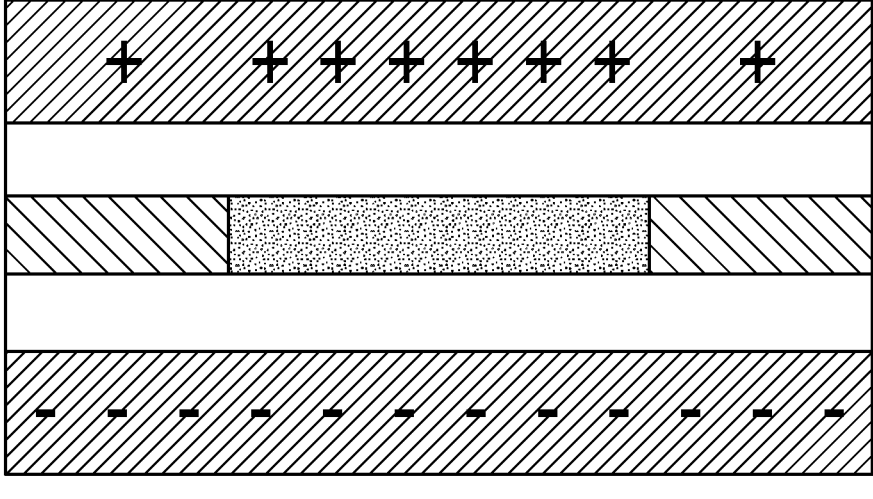
FIGS. 2C and 2D illustrate schematic diagrams describing charge distribution in the circle C in FIGS. 2A and 2B respectively.
Figure 2D:
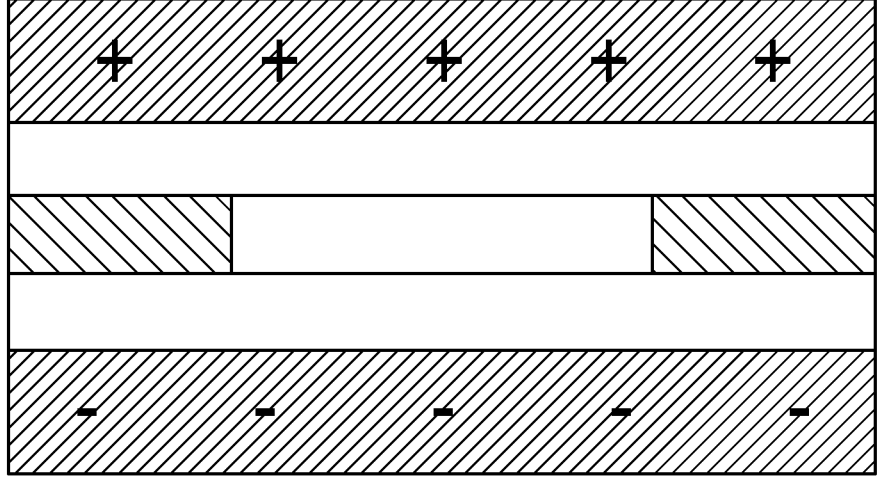

FIGS. 2A and 2B illustrate sectional and top-down views of a sensor according to a "parallel plate" embodiment of the present disclosure during sample collection. FIGS. 2C and 2D illustrate schematic diagrams describing charge distribution in the circle C in FIGS. 2A and 2B, respectively. The sensor is attached on skin 200 using an adhesive material such as a tape 201. The sweat collection area 202 is defined by the inner area of the adhesive tape 201. The sweat 203 sequentially passes through the inlet 181, the microfluidic channel 182, and the outlet 183. If the leading end of the sweat 203 reaches to the outlet 183, the sweat sensor may be switched with a new one. A read-out circuit 190 detects the sweat rate by continuous monitoring of the capacitance between the top 120 and bottom 160 parallel plates. Because the sweat 203 has higher relative permittivity than the air, the capacitance of between the top 120 and bottom parallel plate 160 increases as the sweat collector 180 is filled with the sweat 203, as illustrated in FIGS. 2C and 2D. The read-out circuit 190 may have a wireless transceiver (e.g., Bluetooth, Wifi, radio-frequency identification (RFID), near field communication (NFC) and so on) and thus may wirelessly transmit its measurement to a user. The user can monitor the sweat rate in real-time using a smart phone, a tablet, or a laptop. The measured sweat rate may be stored in a cloud server.

Figures 3A, 3B, 3C, 3D:
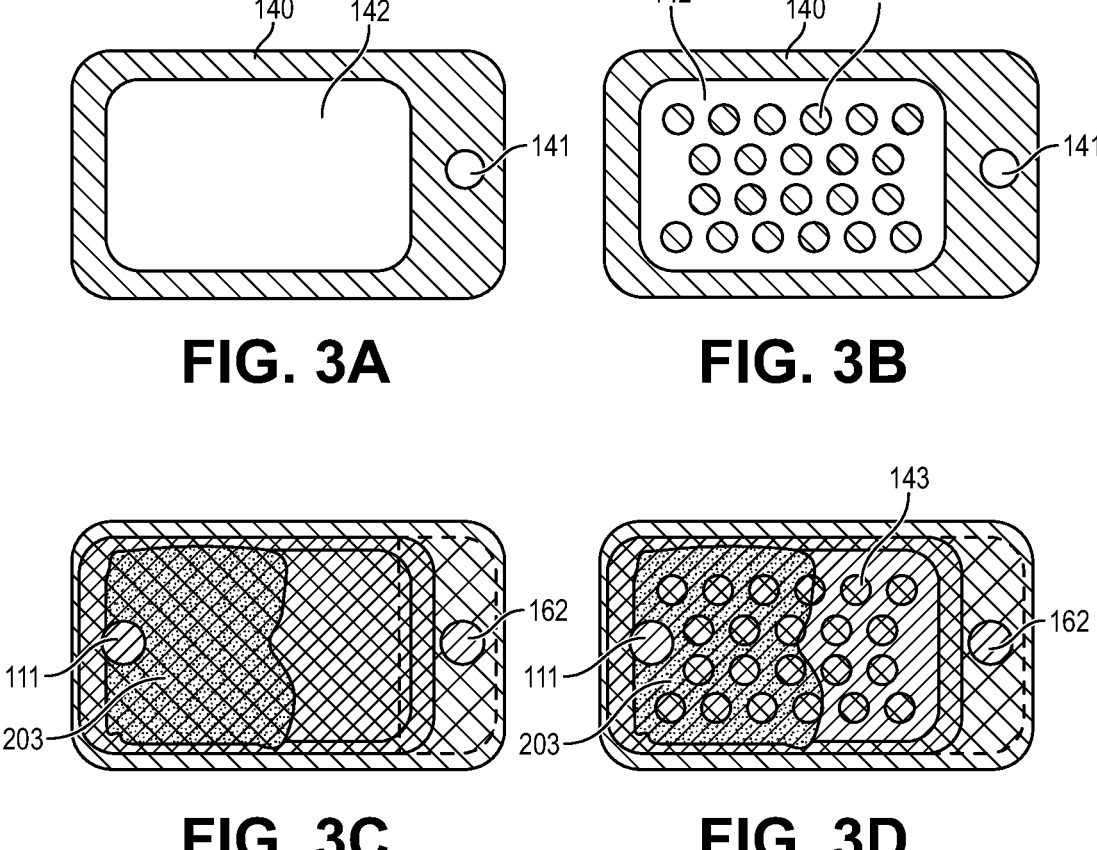
FIGS. 3A-3D illustrate top-down views of a sweat rate sensor having cavity-type microfluidic channel.

FIGS. 3A-3D illustrate top-down views of a sweat rate sensor having cavity-type microfluidic channel. FIGS. 3A and 3B illustrate top-down views of supporting layers of the devices having the cavity-type sweat collector with no post, as in FIG. 3A and posts, as in FIG. 3B. FIGS. 3C and 3D illustrate top-down views of the sweat rate sensor during operation. The cavity-type microfluidic device with no posts is illustrated in FIG. 3C and with posts in FIG. 3D. As the sweat 203 fills the cavity-type microfluidic channel, the capacitance between the top 120 and bottom parallel 160 plates increases. The embodiment of FIGS. 3A-3D is a cavity-type sweat sensor having two parallel plates and microfluidic channels. Depending on the pattern 142 in the supporting layer 140, the sweat collector 180 and the microfluidic channel 182 may have different shapes. The device shown in FIG. 3A has a cavity-type sweat collector 180, which may make the flow resistance of the microfluidic channel 182 lower compared to the device shown in FIGS. 8 and 9. As the sweat 203 fills the cavity, as illustrated in FIG. 2C, the capacitance between the top and bottom parallel plates increases. In order to prevent potential deformation caused by an external pressure, the supporting layer can include posts 143 shown in FIGS. 3B and 3D.

Figure 4A:
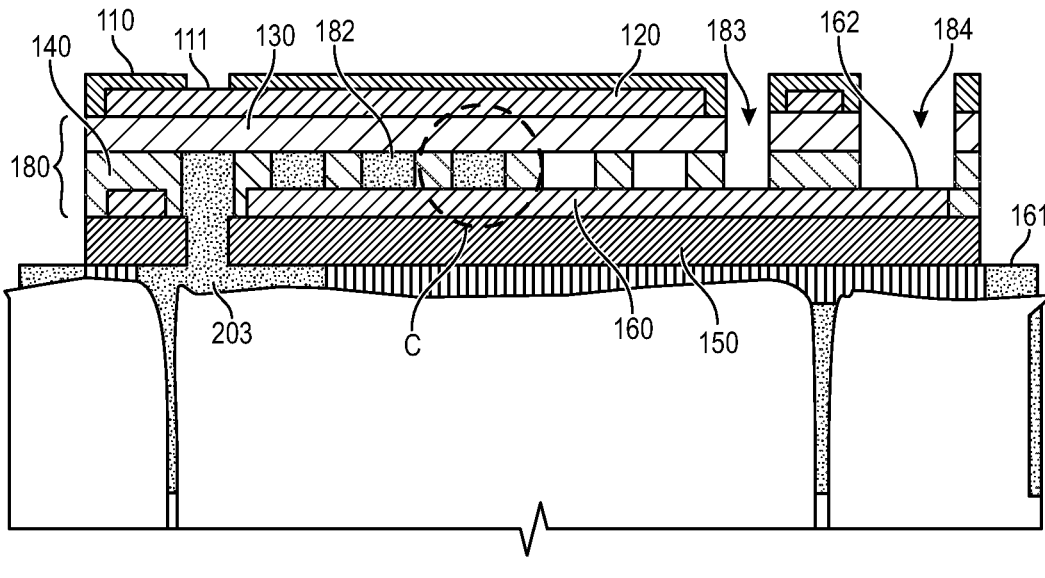
FIG. 4A illustrates a sectional view of the parallel plate embodiment of the sweat rate sensor having a contact between the bottom plate and sweat sample.
Figure 4B:
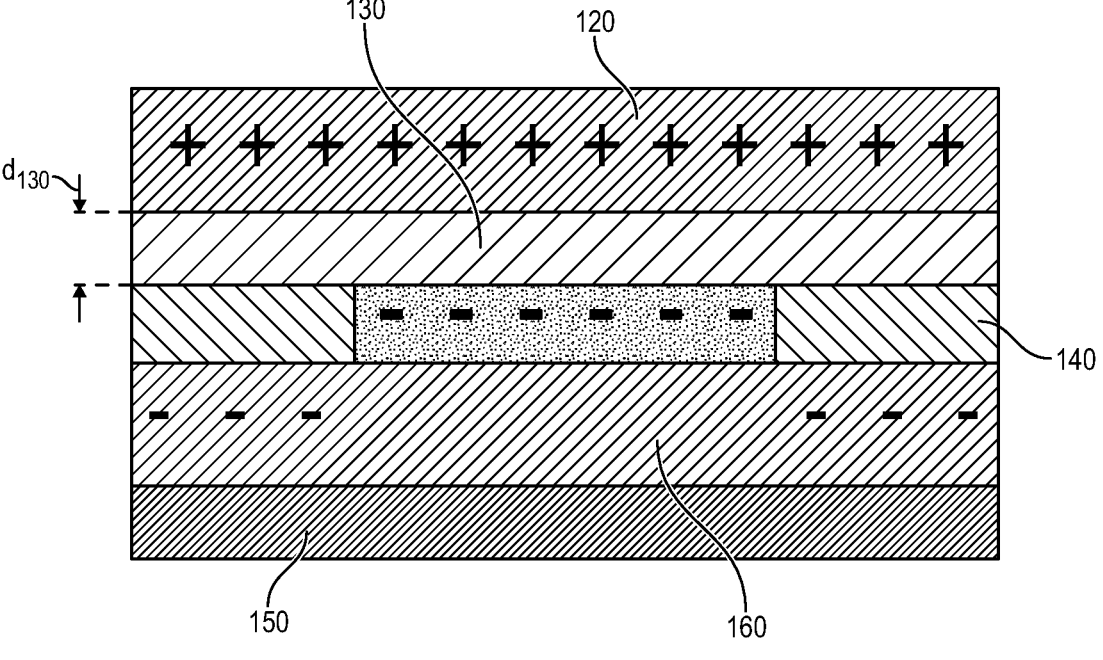
FIG. 4B illustrates a schematic diagram describing the charge distribution in the circle C shown in FIG. 4A.

FIG. 4A illustrates a sectional view of the "parallel plate" embodiment of the sweat rate sensor having a contact between the bottom plate and sweat sample. FIG. 4B illustrates a schematic diagram describing the charge distribution in the circle C shown in FIG. 4A. As another embodiment, the bottom parallel plate 160 faces to the supporting layer 140 and has a contact with sweat 203 when the sweat 203 passes through the microfluidic channel 182. The sweat acts as a movable conductive plate due to abundant electrolytes in the sweat 203 as shown in FIG. 4B. By reducing the thickness d130 of the top substrate 130, the device shown in FIGS. 4A and 4B can achieve high sensitivity (a large change in capacitance at the same sweat rate) compared to the device shown in FIGS. 8 and 9.

The "parallel plate" embodiments described above can be formed with a number of materials and fabrication processes known to or conceivable by one of skill in the art. Below are examples of such materials and fabrication processes. These examples are not meant to be considered limiting and are included to further illustrate the disclosure. The top and bottom insulating layer can be formed from non-conductive flexible materials. The top and bottom insulating layers can be formed by a deposition process or a spin or spray coating process. The top and bottom insulating layers are then patterned by a commercial laser cutting or a wet/dry etching process. The top and bottom insulating layers can be also patterned by a shadow mask process during the deposition process. Also, an adhesive polymer could be employed as the layers.

The top and bottom parallel plate can be formed from a conductive material (e.g., metal, indium tin oxide, conductive polymer, conducting ink, or combination thereof). The layers can be formed by a spin coating, a spray coating, or a deposition process (e.g., physical vapor deposition, screen printing) and then patterned by a wet/dry etching process and a laser engraving process. Also, the layer can be also patterned by a shadow mask process during the deposition process.

The top and bottom substrate layers can be formed from a flexible plastic substrate. The substrate can be cut and patterned by a mechanical cutter or a laser cutter. The supporting layer can be formed from a flexible plastic or a double-sided adhesive polymer. The supporting layer can be patterned by a mechanical cutter or a laser cutter. When the supporting layer material is not a double-sided adhesive polymer and needs to be assembled with the top and bottom, a double-sided tape may be employed. These materials and fabrication methods can also be applied to other embodiments of the present disclosure.

FIGS. 5A-5D illustrate perspective views of a prototype device according to the "parallel plate" embodiment in present disclosure. The prototype is manufactured by a laser cutter and physical vapor deposition (PVD) process. In this exemplary prototype, the top and bottom insulating layers are formed from a commercial one-sided adhesive polymer that is employed and patterned by a laser cutter. The top and bottom parallel plate and substrates are formed from commercially available PET (Polyethylene Terephthalate) substrates deposited by ITO (indium tin oxide). The ITO layers for the top and bottom parallel plate are patterned by a laser engraving process. The PET substrates for the top and bottom substrate are cut by a laser cutter. A commercial double-sided adhesive polymer is patterned by a laser cutter. All layers are easily assembled.

Figures 5A, 5B, 5C, 5D:
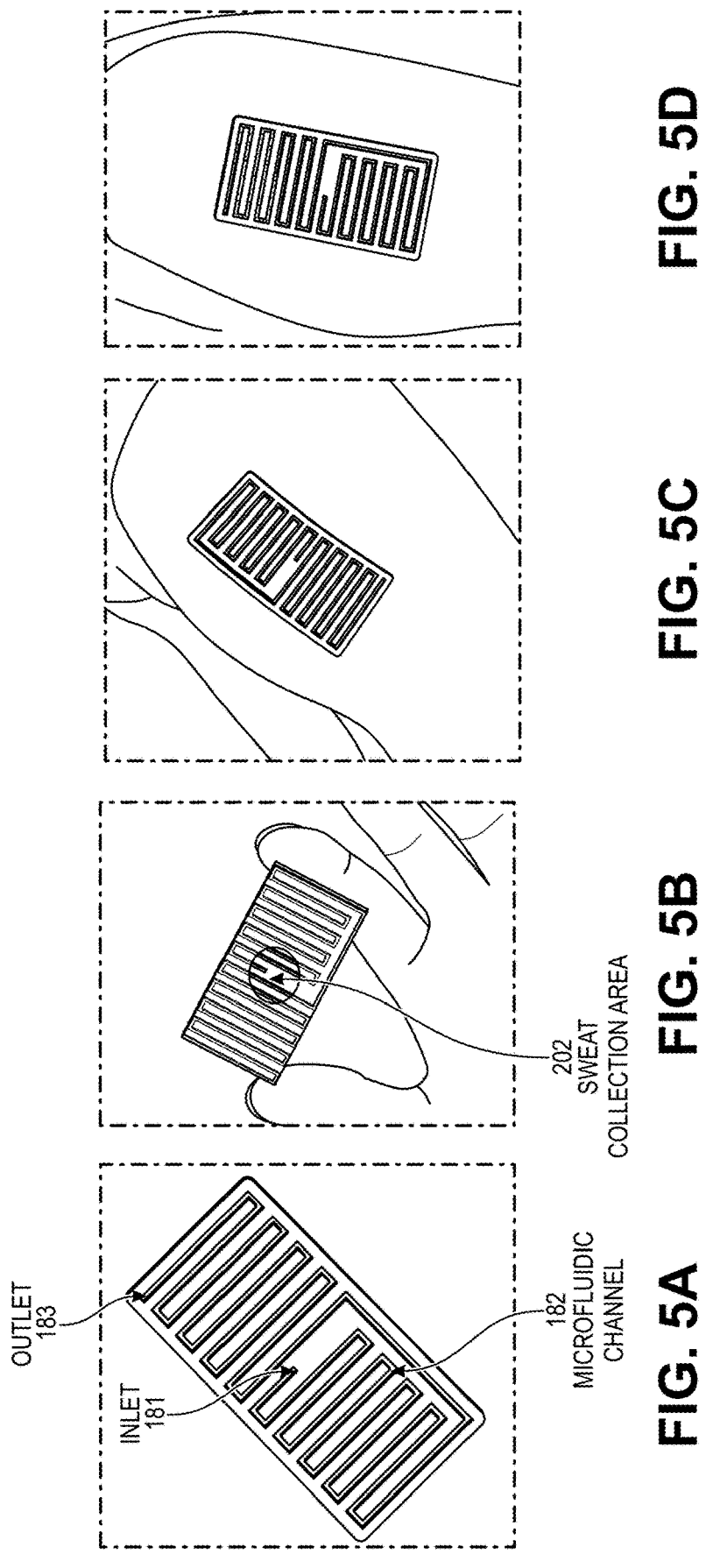
FIGS. 5A-5D illustrate perspective views of a prototype device based on the parallel plate embodiment of the sweat rate sensor according to the present disclosure.

During trials of the prototype, the device successfully collected the sweat sample into the microfluidic channel illustrated in FIGS. 5C and 5D. In this preliminary test, a subject was asked to spin a stationary bike at 100 W of exercise intensity for 30 minutes. To visually check the sweat in the microfluidic channel, the inlet was coated by a blue dye which was dissolved by the sweat during exercise.

Figure 6A:
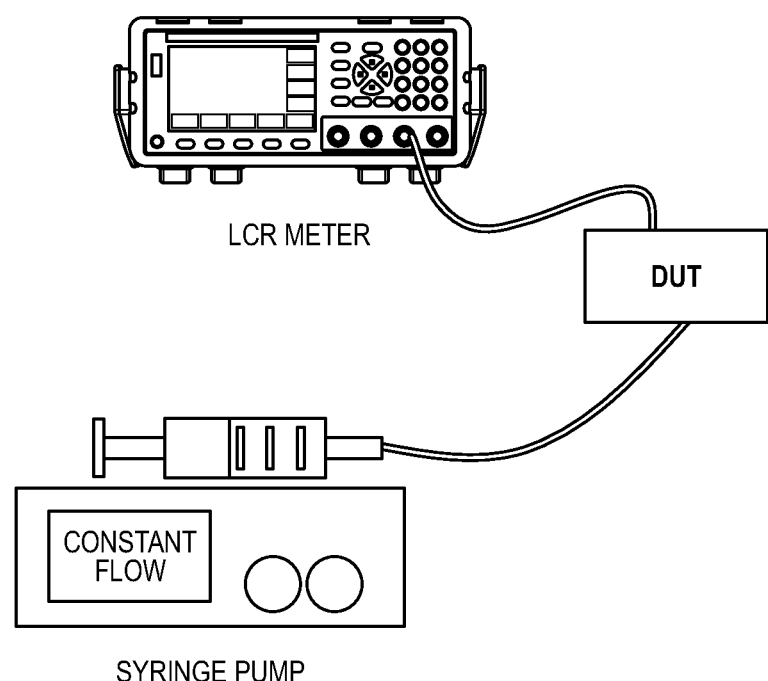
FIGS. 6A and 6B illustrate an experimental setup to measure changes in capacitance depending on sweat volume.
Figure 6B:
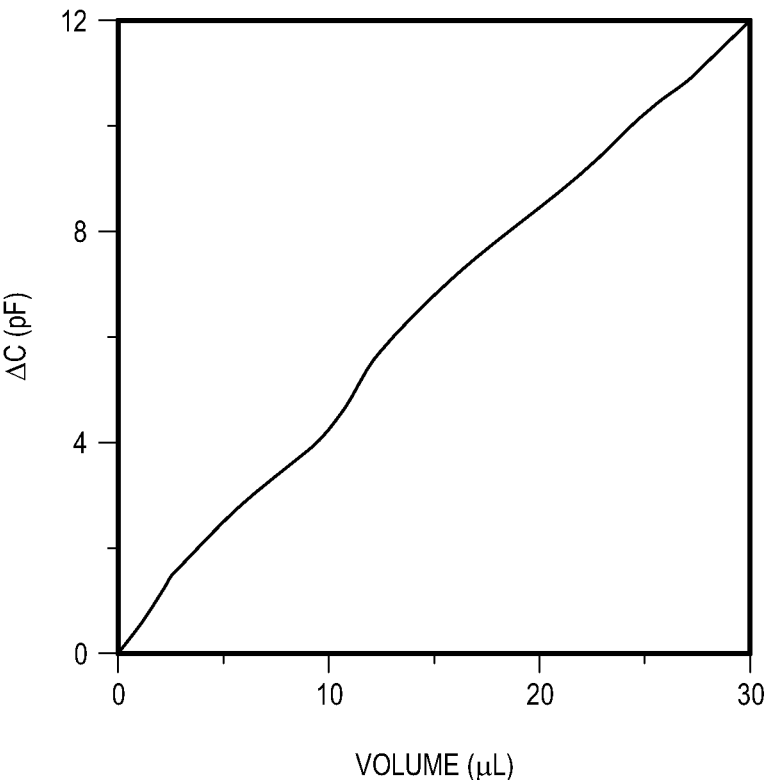

FIGS. 6A and 6B illustrate an experimental setup to measure changes in capacitance depending on sweat volume. In this preliminary test, the changes in capacitance of the sweat rate sensor were measured by a LCR meter when 10 mM of NaCl solution was introduced to the device by a syringe pump, as illustrated in FIG. 6A. FIG. 6B shows a graphical view of a change in capacitance depending on the sweat volume in the sweat rate sensor.

Figure 7A:
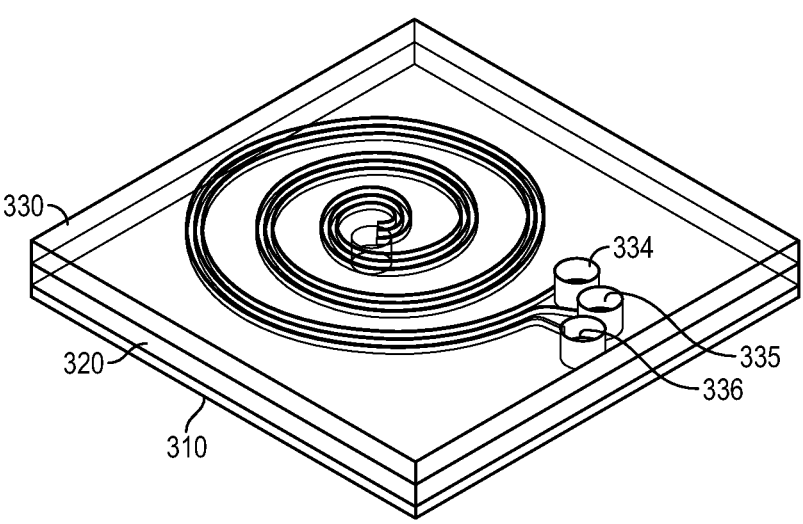
FIGS. 7A-7E illustrate views of a structure and working principles of a "liquid metal" embodiment of the sweat rate sensor.
Figure 7B:
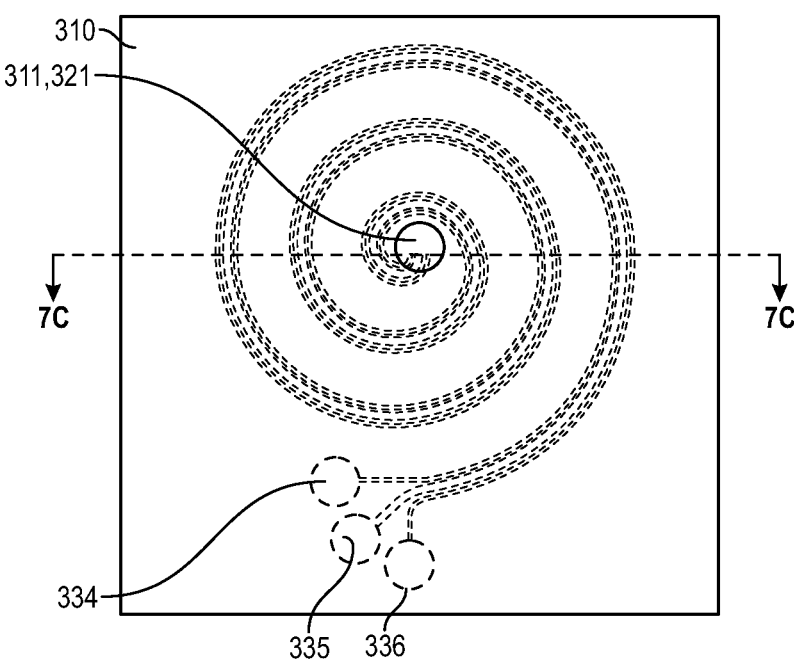
Figure 7C:
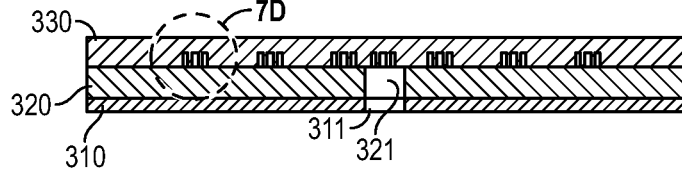
Figure 7D:
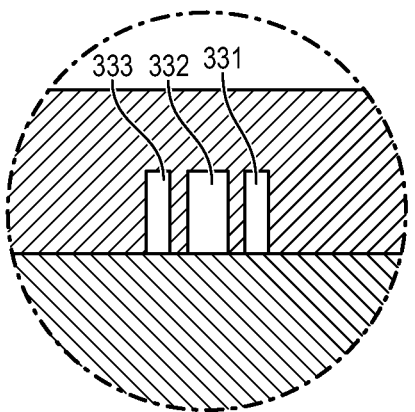
Figure 7E:
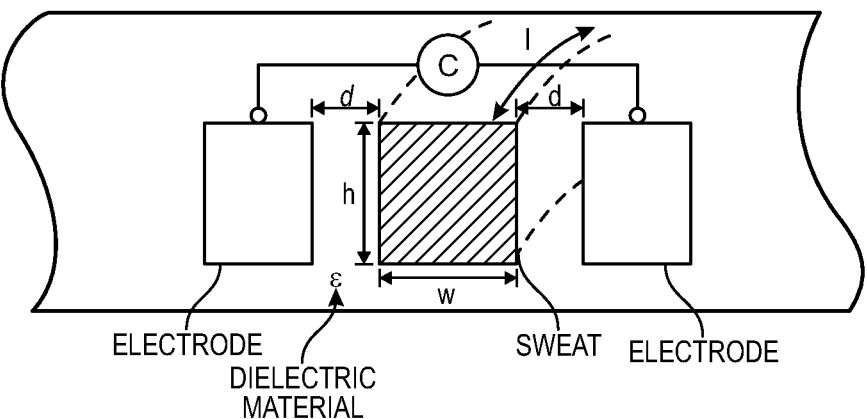

FIGS. 7A-7E illustrate views of a structure and working principles of a sweat rate sensor, according to a "liquid metal" embodiment of the present disclosure. FIG. 7A illustrates a 3D-view of the sweat sensor showing three separate layers bonded together: the bottom double-sided adhesive tape 310, the middle PDMS sealing layer 320, and the top PDMS microchannel layer 330. FIG. 7B illustrates a bottom-view showing the sweat inlet 311 and 321 guiding the sweat into to the sweat microchannel. FIG. 7C illustrates a cross-sectional view. FIG. 7D illustrates a detail view showing the location of the sweat microchannel 332 at the middle of the two parallel liquid metal micro-electrodes alongside 331 and 333. FIG. 7E illustrates an equivalent electrical circuit model to measure the capacitance of the sensor. The design parameters are the channel height (h), the channel width (w), the channel length (l), and the distance between channels (d). The insulation medium between the sweat channel and the electrode channels has relative permittivity $\varepsilon_r$.

One unique property of the sweat sensor of the present disclosure is that the microchannel collecting sweat and the two microelectrodes are placed in the same plane/layer 330. The position of the microchannel layer 330 and the sealing layer 320 can be swapped. The inlet of sweat is defined by the opening on the double-sided adhesive tape 311 connecting the opening on the middle PDMS sealing layer 321. The centers of these two openings are aligned vertically such that the openings are fully covered at the inlet of the sweat microchannel on the top PDMS microchannel layer, as illustrated in FIG. 7C. The top PDMS microchannel layer has three openings: the sweat outlet (335) and two terminals (334 & 336) for electrical connections. The capacitance is measured in real time between these two electrode terminals 334 and 336 as shown in FIG. 7E. The amount of sweat filling the microchannel changes the overall dielectric medium so that the capacitance changes accordingly. The slope of capacitance changes will be converted to the corresponding flow rates using calibration curves in respect to the filling time lapsed.

Figure 8A:
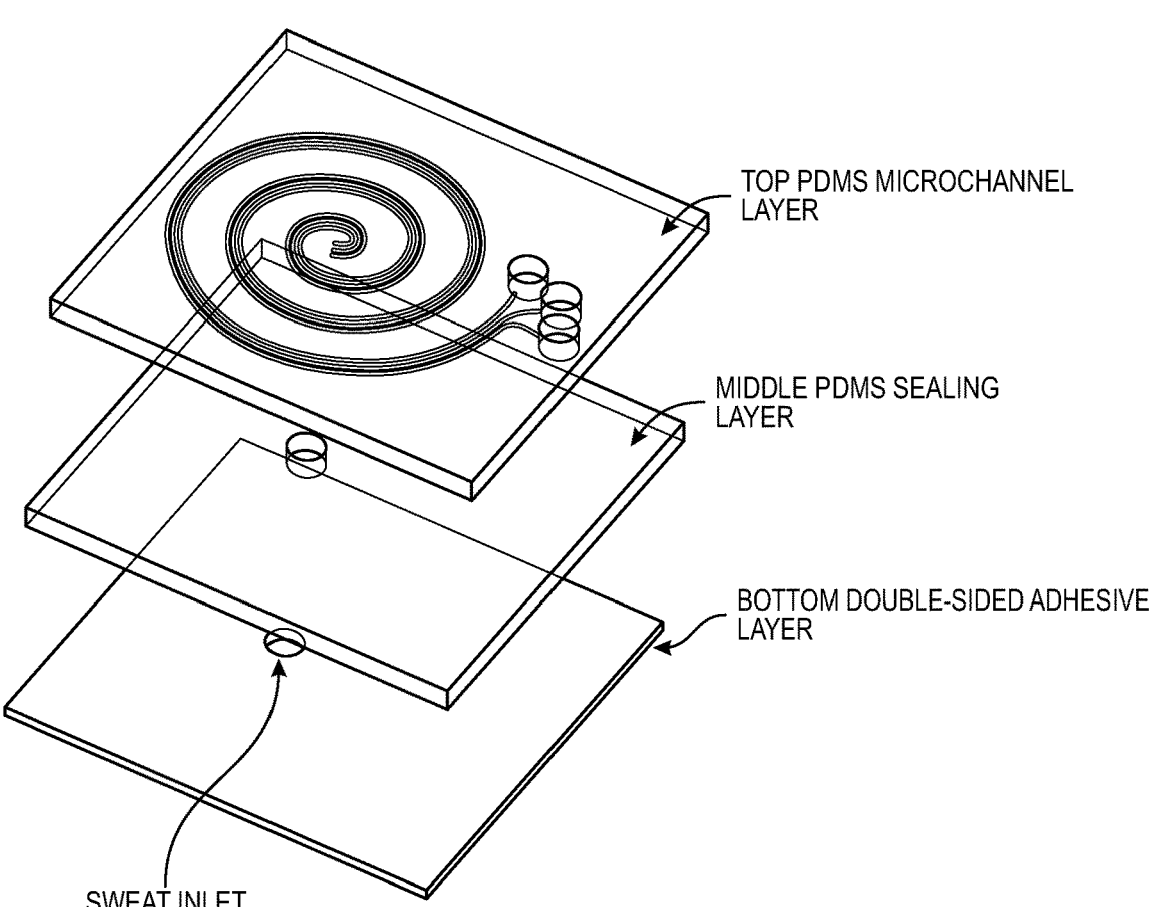
FIG. 8A illustrates an exploded view of the "liquid metal" embodiment of the sweat rate sensor showing three separate layers, according to an embodiment of the present disclosure.
Figure 8B:
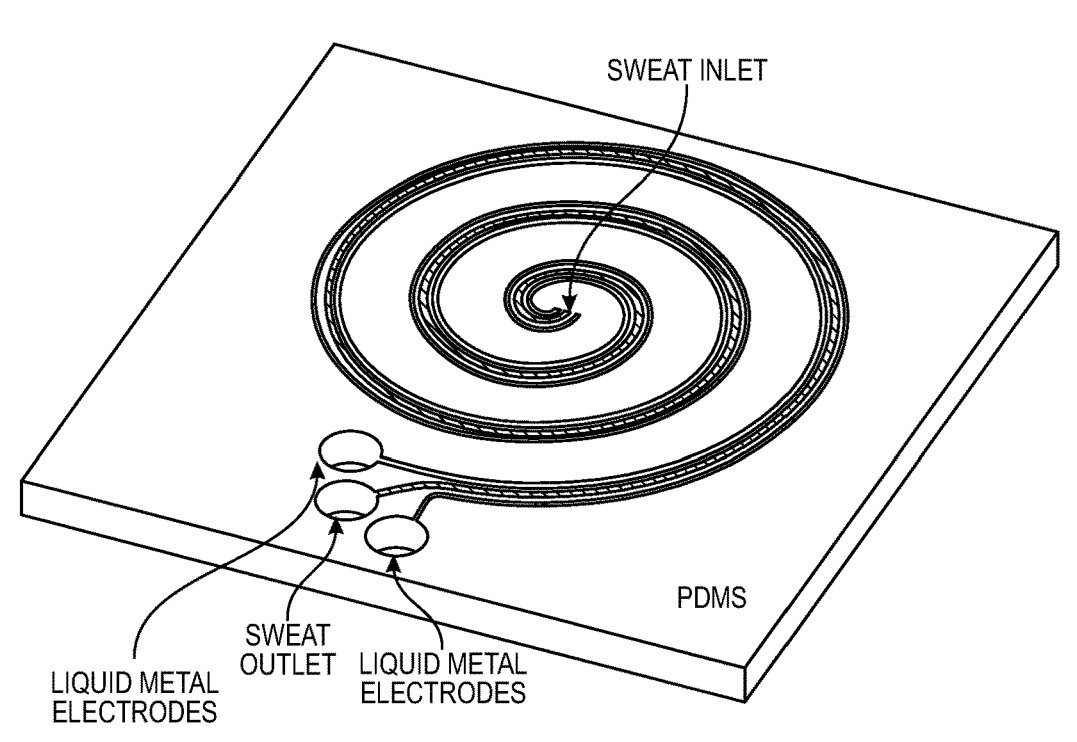
FIG. 8B illustrates a detailed view of the PDMS microchannel layer showing the sweat microchannel (center) and two side electrode microchannels.

FIG. 8A illustrates an exploded view of the sweat sensor showing three separate layers, according to the "liquid metal" embodiment of the present disclosure. FIG. 8B illustrates a detailed view of the PDMS microchannel layer showing the sweat microchannel (center) and two side electrode microchannels. FIG. 8A shows the three separate layers of the sensor. The top PDMS microchannel layer 330 is bonded irreversibly to the middle PDMS sealing layer 320 (e.g., by plasma treatment). The bottom double-sided adhesive tape 310 is bonded to the middle PDMS layer 320 by a strong silicone adhesive. The other side of the double-sided adhesive tape is attached on to the skin of human body by a biocompatible adhesive. The sweat inlet diameter 311 and 321 can be varied. The variation depends on the microchannel geometry. The sweat outlet 335 is open to the atmosphere air to reduce the resistance. Its diameters can be changed depending on the practical activities. The distance d between the sweat channel 332 and the electrode channels 331 and 333 is defined by the desired measurement resolution and the actual working time. Different liquid metals (or alloys) can be used to fill the electrode microchannels 331 and 333. The connection terminals 334 and 336 are formed at the end of the electrode microchannels as shown in FIG. 8B. The external electrical wires are connected to these terminals for real-time capacitive measurements. The sweat sensor is capable of conforming to the human skin curvatures due to its flexibility, simplicity, and durability.

The embodiment of FIGS. 8A and 8B includes 3 layers: a PDMS microchannel layer, a PDMS sealing layer, and a double-sided adhesive tape layer. The sweat microchannel and the two electrode microchannels are in the same plane. The inlet of sweat microchannel is contacted with the skin, and the outlet of sweat microchannel is on the opposite side. The PDMS microchannel is fabricated by a standard soft lithography process. A thin PDMS membrane may be bonded irreversibly to the PDMS microchannel layer to seal the microchannel. The liquid metal is inserted into the electrode microchannels at their openings. The electrical wires are connected to the device at the electrode terminals. The double-sided adhesive tape is used to attach the device to skin.

Figure 9A:
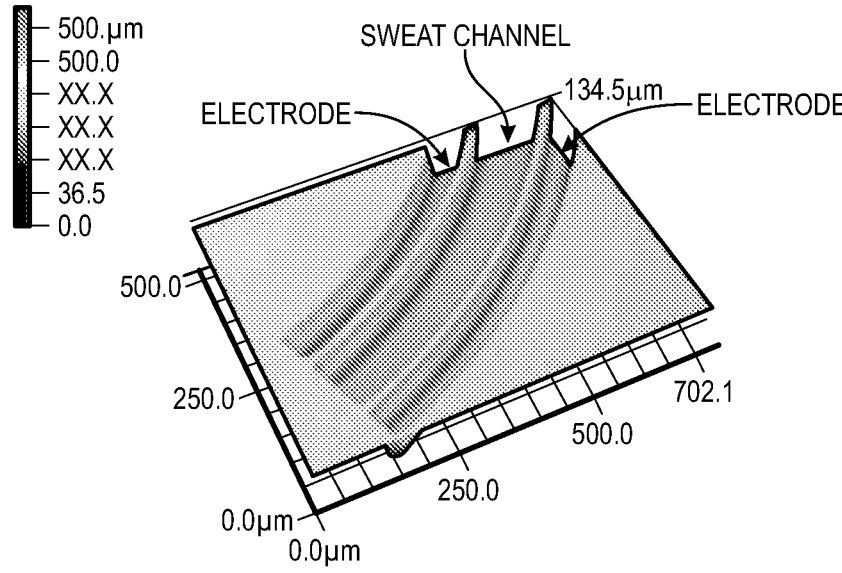
FIG. 9A illustrates a profile image of the "liquid metal" embodiment of the sweat rate sensor showing PDMS channels showing a sweat channel in the center and two electrode channels running parallel on two sides.
Figure 9B:
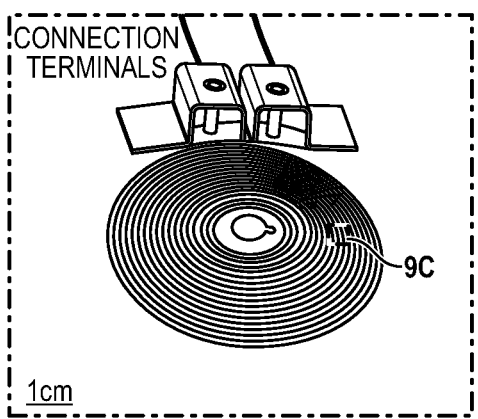
FIG. 9B illustrates an image of a wearable sweat rate sensor attached on a user's forearm using double-sided adhesive tape. The sweat is colored using (e.g., blue) dye powder placed at the inlet of the microfluidic channel.
Figure 9C:
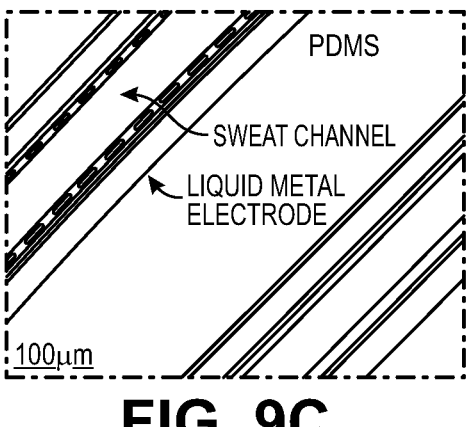
FIG. 9C illustrates an optical image showing the liquid metal electrodes (black channels) and the sweat microchannel located in between the two electrodes (empty channel).

FIG. 9A illustrates a profile image of PDMS channels showing a sweat channel in the center and two electrode channels running parallel on two sides. FIG. 9B illustrates an image of a wearable "liquid metal" sweat rate sensor attached on the forearm using double-sided adhesive tape. The sweat is colored using (e.g., blue) dye powder placed at the inlet of the microfluidic channel. FIG. 9C illustrates an optical image showing the liquid metal electrodes (black channels) and the sweat microchannel located in between the two electrodes (empty channel).

Figure 10A:
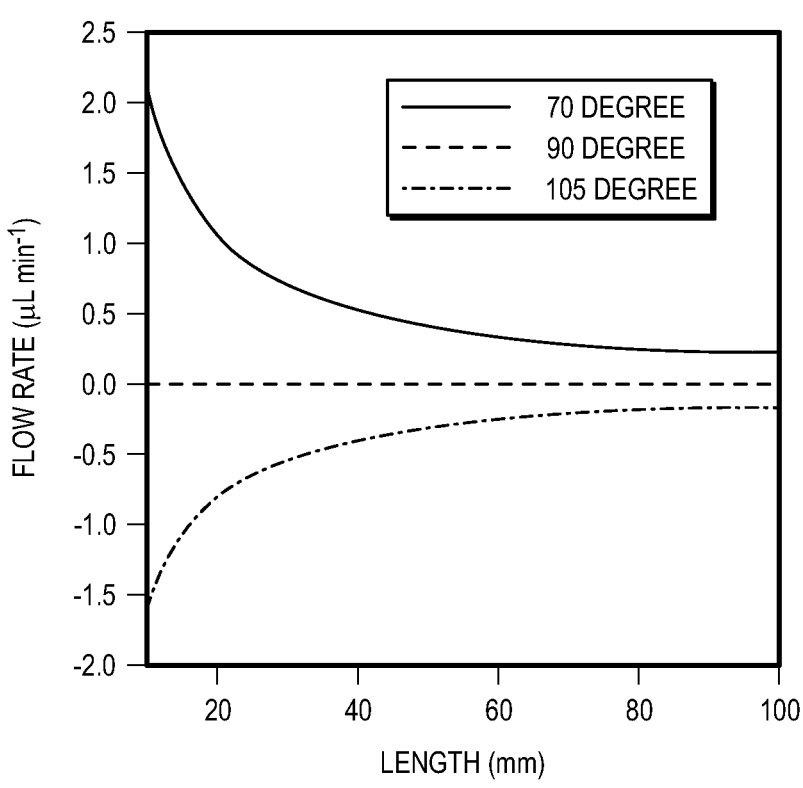
FIGS. 10A-10D illustrate graphical views of validation at different flow rates and salt concentrations of the "liquid metal" embodiment of the sweat rate sensor.
Figure 10B:
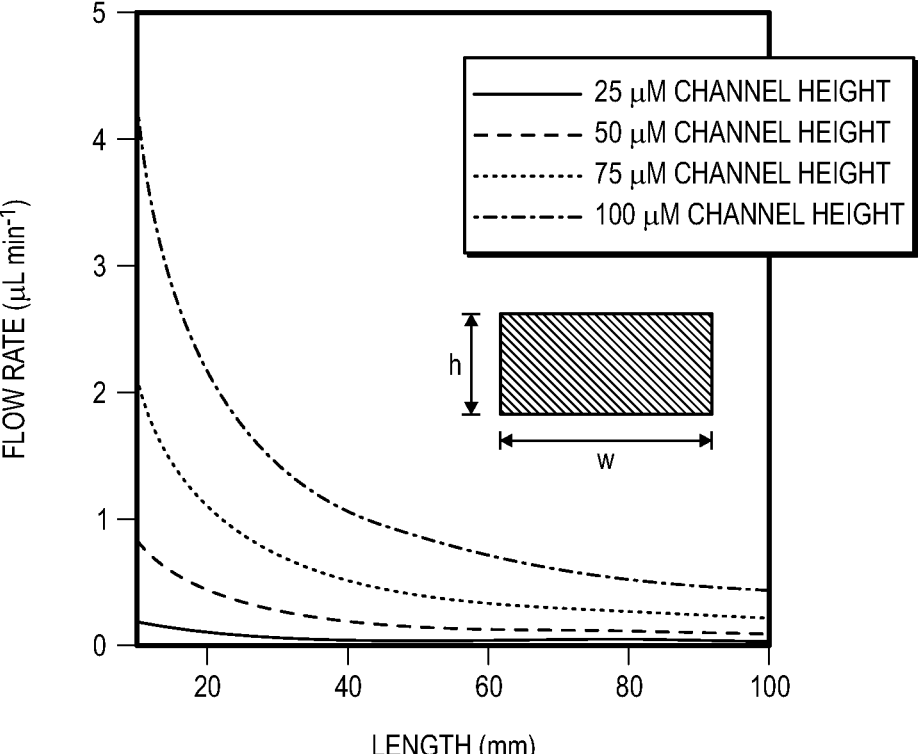

To effectively collect the sweat into the microchannel, the contact angles between sweat and microchannel surface (e.g., PDMS) can be optimized for different channel geometries, as illustrated in FIGS. 10A and 10B. Surface modification can be used to maintain a hydrophilic surface, minimizing the hydrodynamic resistance of the microchannel.

Figures 10C, 10D:
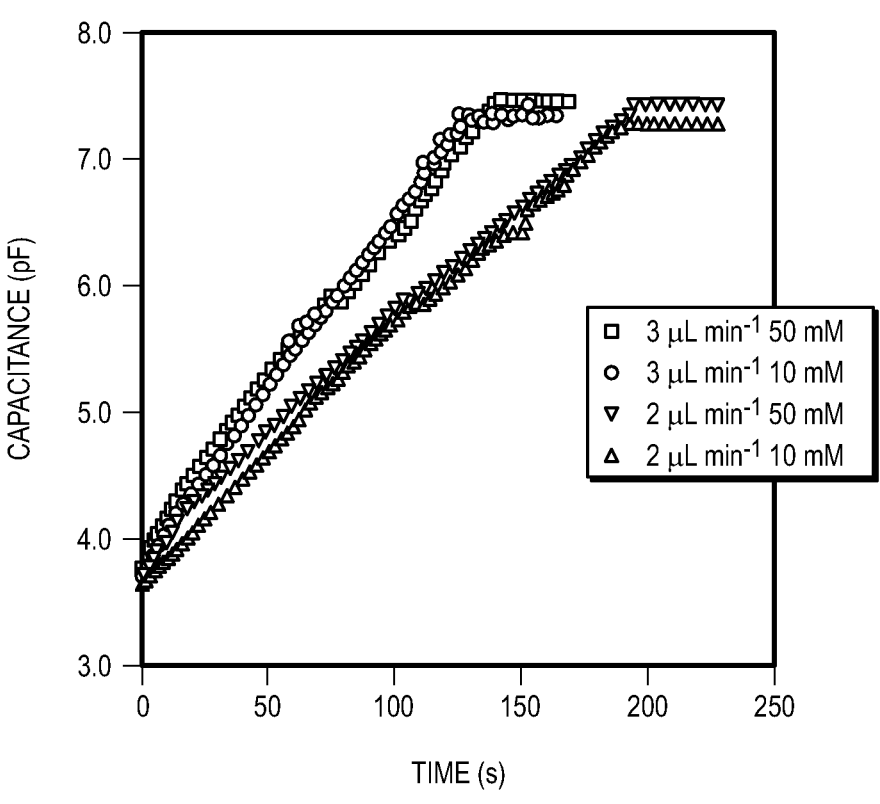

FIGS. 10A-10D illustrate graphical views of validation at different flow rates and salt concentrations of the sweat sensor. The capacitance, which is proportional to the sweat volume in the device, increases (e.g., linearly at a constant flow rate) and may be independent of salt concentration. By converting the calibrated capacitances to volume, the sweat rate can be measured in real time. More particularly, FIG. 10A illustrates the dependency on the contact angles of the flow rate inside microchannel. FIG. 10B illustrates the dependency on the microchannel's geometry of the flow rate inside microchannel. FIG. 10C illustrates the linear increases in capacitance corresponding to the constant flow rates of NaCl solutions entering the microfluidic channel of the device. The tests performed with 10 mM and 50 mM NaCl solution. FIG. 10D illustrates the tests performed with 100 mM NaCl solution on another device.

Figure 11A:
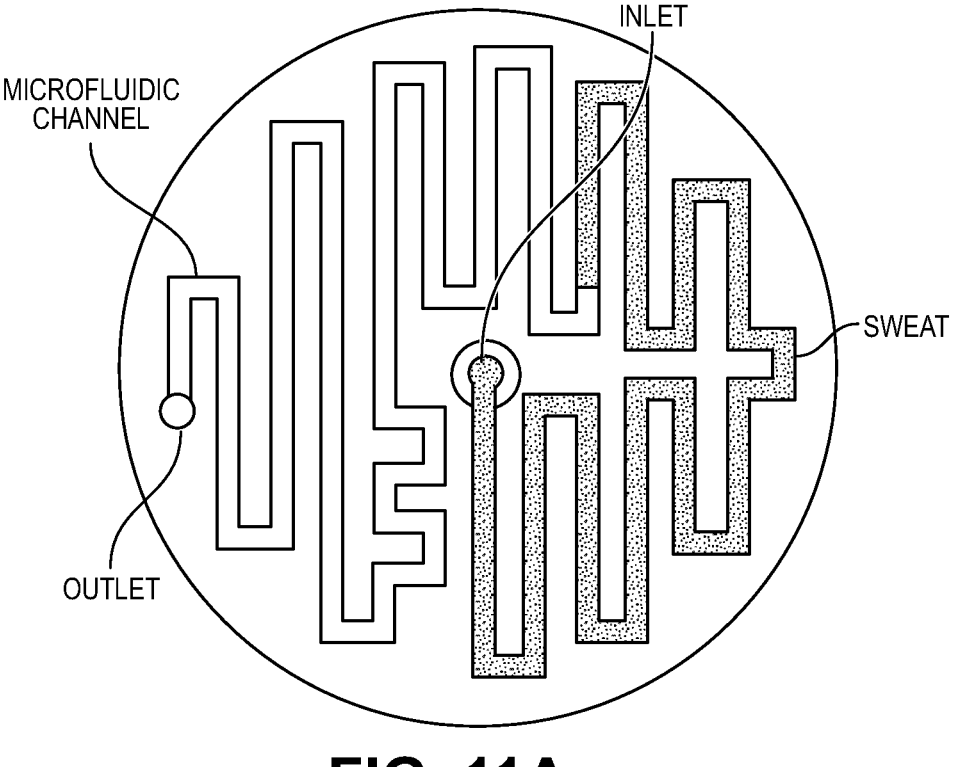
FIG. 11A illustrates a schematic diagram of the "parallel plate" embodiment of the sensor which can continuously measure sweat rate in real time.
Figure 11B:
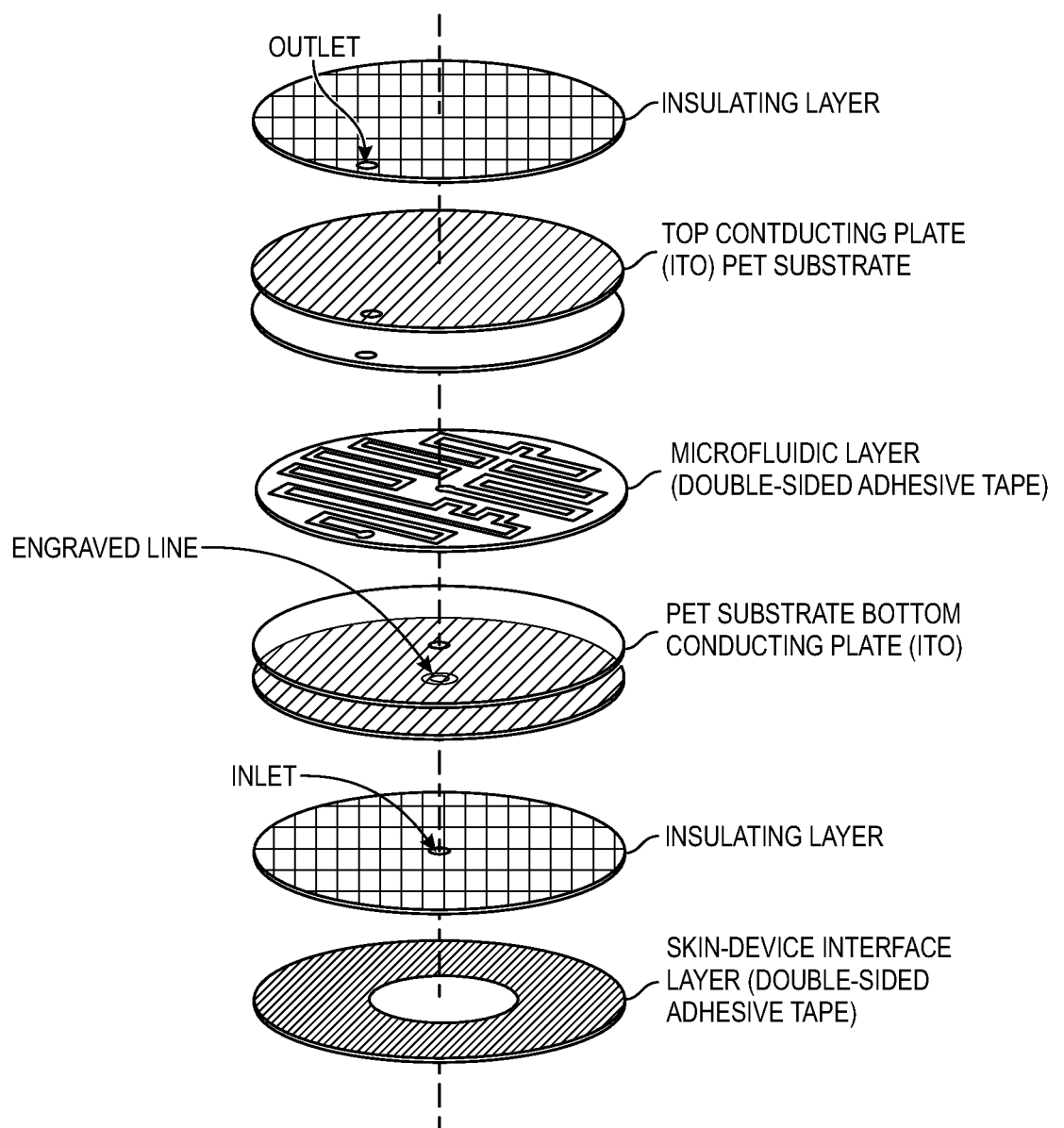
FIG. 11B illustrates a top-down view of the sensor.
Figure 11C:
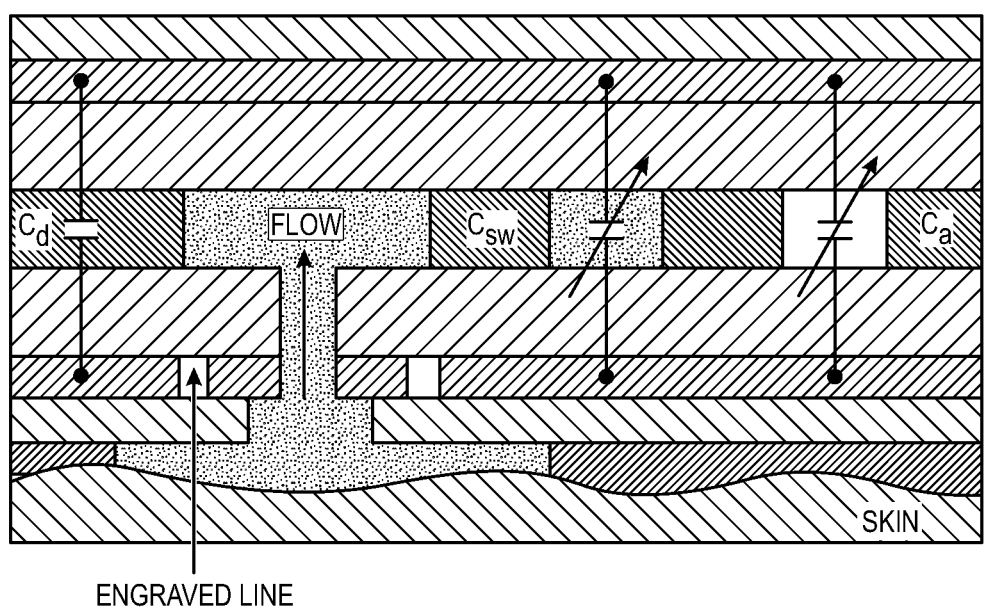
FIG. 11C illustrates a cross-sectional view of the sensor and equivalent electrical components ($C_{sw}$: capacitance of the area of the microfluidic channel filled with sweat, $C_a$: capacitance of the area of the microfluidic channel filled with air, $C_d$: capacitance of the other area).
Figure 11D:
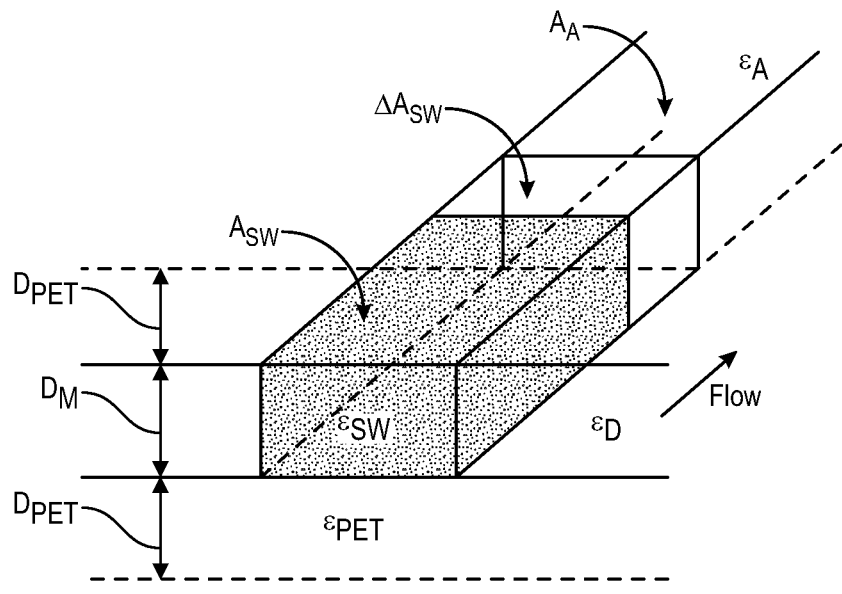
FIG. 11D illustrates a change in the area ($A_{sw}$) of the microfluidic channel filled with the sweat as the sweat flows through the channel.

FIG. 11A illustrates a schematic diagram of the "parallel plate" sensor which can measure the sweat rate continuously in real time. FIG. 11B illustrates a top-down view of the sensor. FIG. 11C illustrates a cross-sectional view of the sensor and equivalent electrical components ($C_{sw}$: capacitance of the area of the microfluidic channel filled with sweat, $C_a$: capacitance of the area of the microfluidic channel filled with air, $C_d$: capacitance of the other area). FIG. 11D illustrates a change in the area ($A_{sw}$) of the microfluidic channel filled with the sweat as the sweat flows through the channel.

In the "parallel plate" embodiment of the present disclosure, the sweat rate sensor includes two (top and bottom) parallel conducting plates formed on a plastic substrate, a microfluidic layer, two insulating layers covering the conducting plates, and a skin-sensor interface layer, as illustrated in FIG. 11A. A microfluidic channel is formed between the top and bottom parallel plates by interposing the microfluidic layer between the two plastic substrates. The inlet and outlet of the microfluidic layer are connected to the holes the top and bottom plate layers. During perspiration, sweat enters through the inlet, and the microfluidic channel is progressively filled, as illustrated in FIGS. 11B and 11C. In this embodiment, thin film ITO is deposited on a PET substrate and used for the top and bottom plates. Due to its transparency, the sweat flow in the fluidic channel is easily visible. The sensor output ($C_s$) is the capacitance between the two plates, as illustrated in FIG. 11C. Initially, the microfluidic channel is empty (filled with air). However, the fluidic channel is filled with the sweat as the sweating started, and the $C_s$ value increases, because the sweat has a much higher permittivity than air.

The device can be modeled by three capacitors in parallel:

$$C_s = C_{sw} + C_a + C_d \tag{1}$$

where $C_s$ is the total capacitance of the sensor, $C_{sw}$, is the capacitance of the part of the microfluidic channel filled with sweat (area=$A_{sw}$, see FIG. 11D), $C_a$ is the capacitance of the part of the channel that is empty (area=$A_a$), and $C_d$ is the capacitance of the sensor where there is no microfluidic channel (area=$A_d$). Note that $A_{sw}+A_a+A_d$ is the total area of the capacitive plates.

Each contribution to the total capacitance can be modeled as three capacitors in series, corresponding to the three dielectrics. Since the area of the channel filled with sweat ($A_{sw}$) increases with time and the area filled with air ($A_a$) decreases in a complementary manner, as illustrated in FIG. 11D, $C_{sw}$ and $C_a$ are dependent on sweat rate and time, while $C_d$ is constant:

$$C_{sw}(t) = \left( \left( \frac{\varepsilon_{PET}\varepsilon_0 A_{sw}(t)}{d_{PET}} \right)^{-1} + \left( \frac{\varepsilon_{sw}\varepsilon_0 A_{sw}(t)}{d_m} \right)^{-1} + \left( \frac{\varepsilon_{PET}\varepsilon_0 A_{sw}}{d_{PET}} \right)^{-1} \right)^{-1} = \tag{2}$$

$$\frac{\varepsilon_{sw}\varepsilon_{PET}\varepsilon_0}{2\varepsilon_{sw}d_{PET} + \varepsilon_{PET}d_m} A_{sw} = \frac{\varepsilon_{sw}\varepsilon_{PET}\varepsilon_0}{2\varepsilon_{sw}d_{PET} + \varepsilon_{PET}d_m} \cdot \frac{\int SR(t)A_c \cdot dt}{d_m}$$

$$C_a(t) = \frac{\varepsilon_{air}\varepsilon_{PET}\varepsilon_0}{2\varepsilon_{air}d_{PET} + \varepsilon_{PET}d_m} \tag{3}$$

$$A_a(t) = \frac{\varepsilon_{air}\varepsilon_{PET}\varepsilon_0}{2\varepsilon_{air}d_{PET} + \varepsilon_{PET}d_m} \cdot \left( A_a(t=0) - \frac{\int SR(t)A_c \cdot dt}{d_m} \right)$$

$$C_d = \frac{\varepsilon_{dt}\varepsilon_{PET}}{2\varepsilon_{dt}\varepsilon_{PET} + \varepsilon_{PET}\varepsilon_{mf}} A_{dt} \tag{4}$$

where SR(t) is the sweat rate ($\mu$L cm$^{-2}$ min$^{-1}$), $A_c$ is the sweat collection area (cm$^2$), $\varepsilon_0$ is the permittivity of free space, $\varepsilon_0$ is the permittivity of free space, $\varepsilon_{PET}$ is the relative permittivity of the PET substrate, $\varepsilon_{sw}$ is the relative permittivity of sweat, $\varepsilon_d$ is the relative permittivity of air, $\varepsilon_d$ is the relative permittivity of the microfluidic template layer, $d_{PET}$ is the thickness of the PET substrate, and $d_m$ is the thickness of the microfluidic layer defined by the double sided tape.

Changes in capacitance are expected to be proportional to the sweat rate, which can be calculated from the slope ($dC_s(t)/dt$) of the capacitance curve obtained from the sweat rate sensor. Taking $A_c=1$ cm$^2$, $d_m=90$ $\mu$m, $d_{PET}=179$ $\mu$m, $\varepsilon_{PET}=3$, $\varepsilon_{sw}=80$, $\varepsilon_a=1$, $\varepsilon_b=8.854\times10^{-12}$ F m$^{-1}$, and defining the units of sweat rate (SR) as μL min⁻¹cm⁻², and the units of slope (dC_S(t)/dt) as pF min⁻¹:

$$\frac{dC_s(t)}{dt} = \tag{5}$$

$$\frac{\varepsilon_{PET}\varepsilon_0 A_C}{d_m}\left(\frac{\varepsilon_{sw}}{2\varepsilon_{sw}d_{PET} + \varepsilon_{PET}d_m} - \frac{\varepsilon_a}{2\varepsilon_a d_{PET} + \varepsilon_{PET}d_m}\right)\cdot SR(t)\square 0.35\cdot SR(t)$$

where $A_c$=1 cm², $d_m$=179 μm, $d_{PET}$=90 μm, =4, $\varepsilon_{sw}$=80, $\varepsilon_a$=1, $\varepsilon_b$=8.854 10⁻¹² F m⁻¹, and the units of the sweat rate (SR) and the slope (dC_S(t)/dt) are μL min⁻¹ and pF min⁻¹, respectively.

Figures 12A, 12B, 12C:
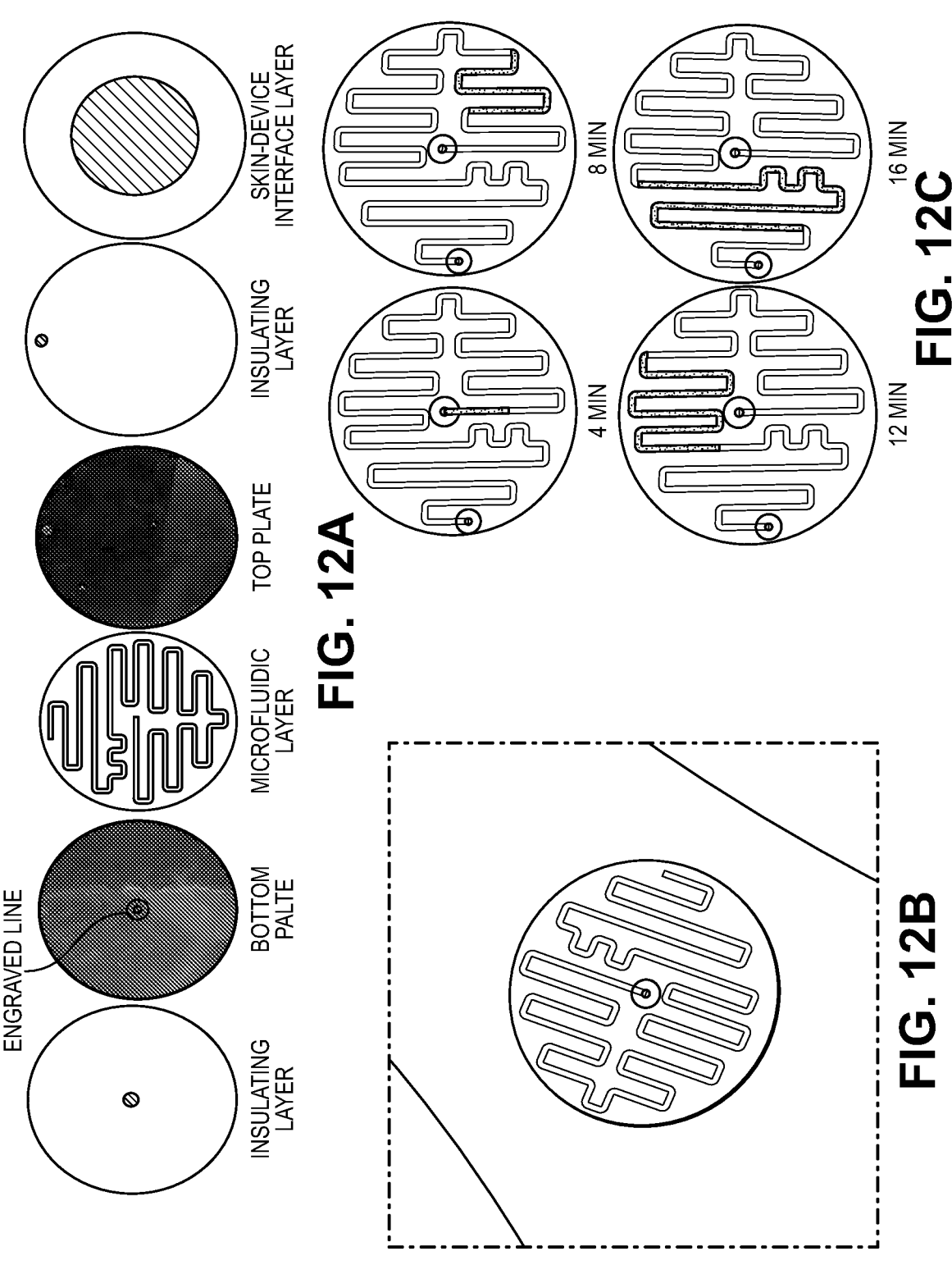
FIGS. 12A-12C illustrate views of a wearable sweat rate sensor, according to the "parallel plate" embodiment of the present disclosure.

FIGS. 12A-12C illustrate views of a manufactured wearable sweat rate sensor, according to the "parallel plate" embodiment of the present disclosure. A consequence of the simple sensor design is that microfabrication and precise alignment between the layers are eliminated. All layers may be cut to size using a commercial laser cutter and manually assembled, as illustrated in FIG. 12A. To electrically isolate the bottom plate from sweat, the ITO film was engraved in a circular pattern a little larger than the inlet of the microfluidic channel, as illustrated in FIGS. 11D and 12A. In this embodiment, the volume of the microfluidic channel was 31.5 μL: total length (l)=350 mm, width (w)=1 mm, and thickness ($d_m$)=90 μm. Typical sweat rates for healthy individuals vary from 0.1 to 1 μL min⁻¹cm⁻² ²², therefore, with these dimensions and a sweat collection area of 0.5 cm², the sensor can be used for more than 60 minutes. Incorporating a dye into the channels allows sweat filling of the sensor to be easily visualized. FIG. 12B illustrates the sensor attached to a forearm after pilocarpine iontophoresis. FIG. 12C shows the sequential images of a sensor while the sensor was filled with sweat.

Figure 13A:
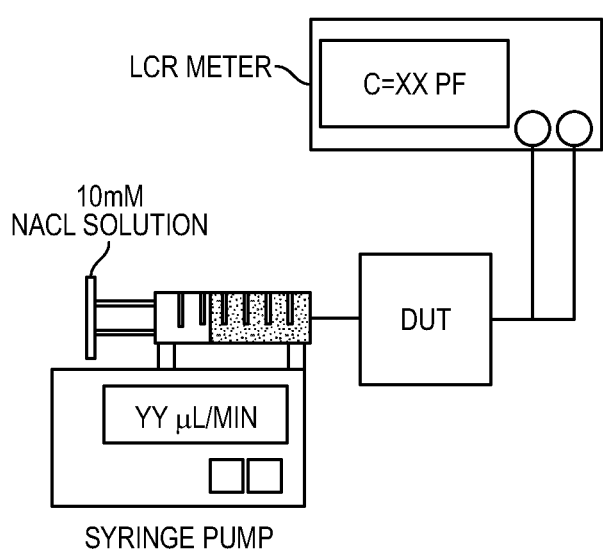
FIG. 13A illustrates a test set-up.
Figure 13B:
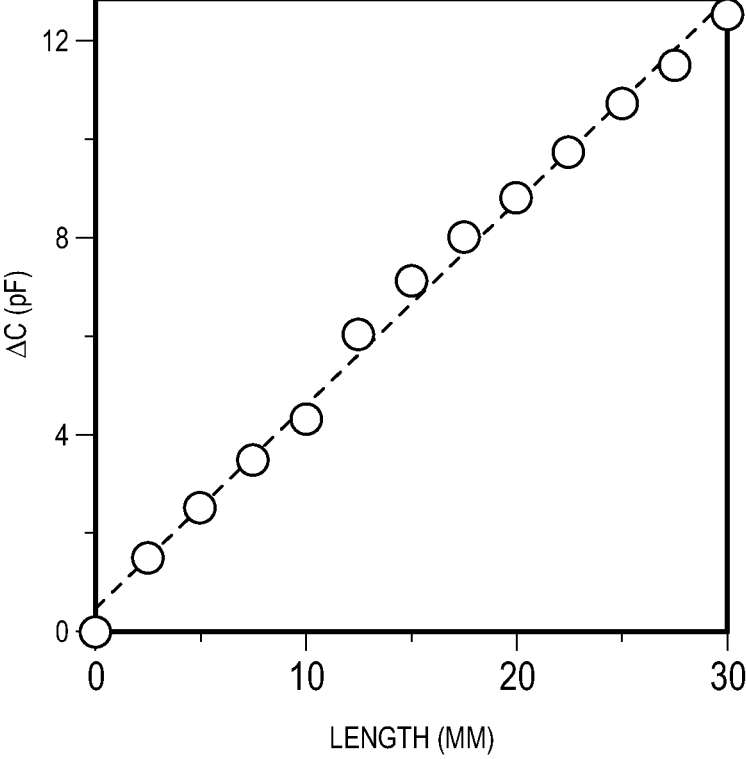
FIG. 13B illustrates a graphical view of a correlation between increases in capacitance ($\Delta C$) and the length of the microfluidic channel filled with the test fluid.
Figures 13C, 13D:
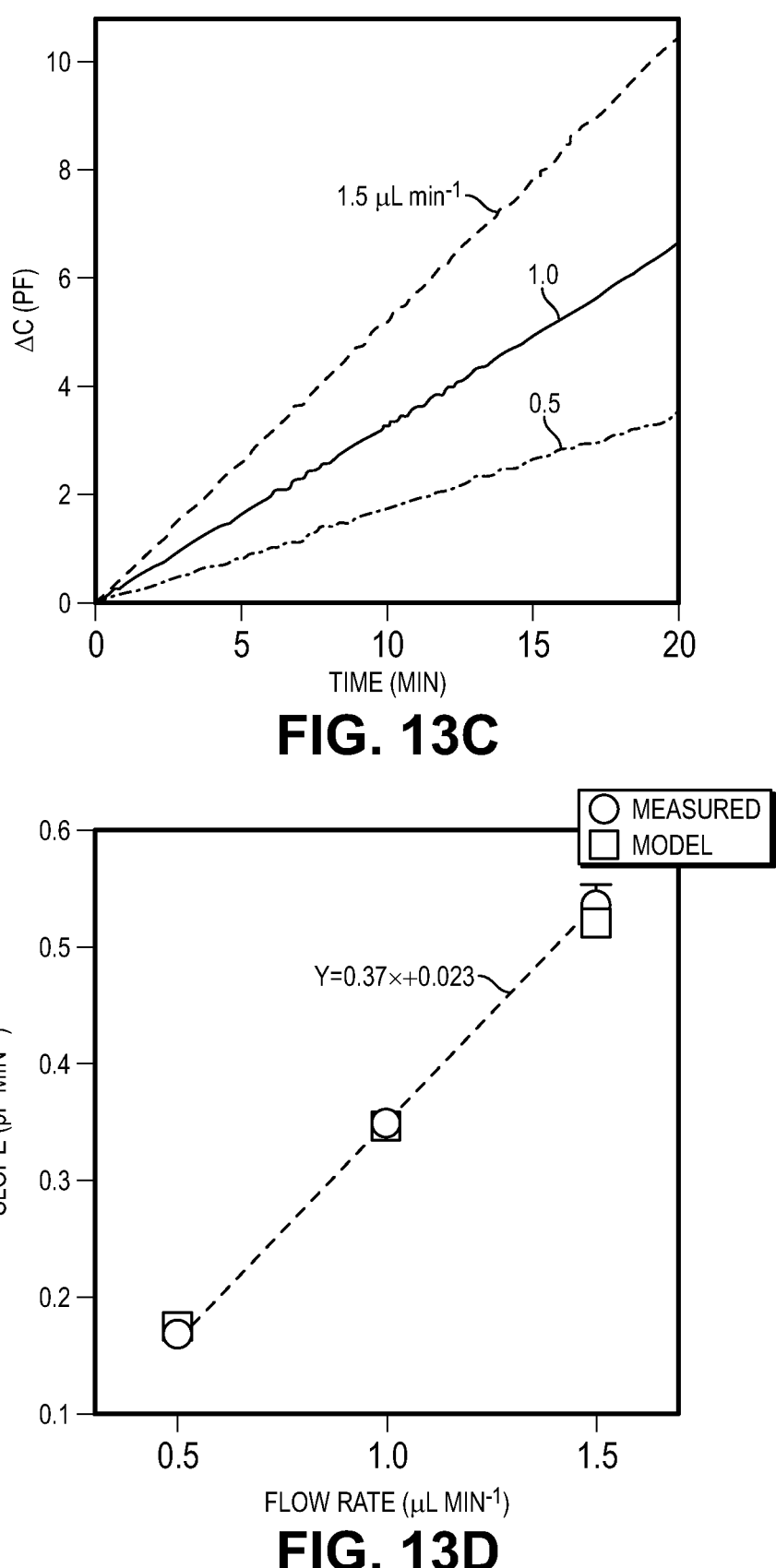
FIG. 13C illustrates a graphical view of changes in capacitance ($\Delta C$) at three different flow rates.
FIG. 13D illustrates a graphical view of a calibration curve obtained from the measurement shown in panel C.

FIG. 13A illustrates a test set-up for validation of sensor performance. FIG. 13B illustrates a graphical view of correlation between increases in ΔC and the length of the microfluidic channel filled with the test fluid. FIG. 13C illustrates a graphical view of changes in capacitance (ΔC) at three different flow rates. FIG. 13D illustrates a graphical view of a calibration curve obtained from the measurement shown in panel B. The measured calibration values agreed with the theoretically calculated values based on Eq. 5. To evaluate the characteristic of the sensor, three different constant flows of 0.5, 1.0 and 1.5 μL min⁻¹ were introduced to the sensor using a syringe pump, and the changes in capacitance of the sensor were monitored by a LCR meter, as illustrated in FIG. 13A. The capacitance change increased linearly with the fraction of the microfluidic channel filled with fluid and was independent of flow rate, as illustrated in FIG. 13B. The slopes of the plots at 0.5, 1.0, 1.5 μL min⁻¹ were 0.044, 0.045, and 0.044 pF mm⁻¹, respectively, and the average Pearson correlation coefficient was 0.9996±0.0003. At constant flow rate, the capacitance change increased linearly with time during filling, as illustrated in FIG. 13D. Since variation among devices was very small, sensor calibration may be omitted.

Figure 14A:
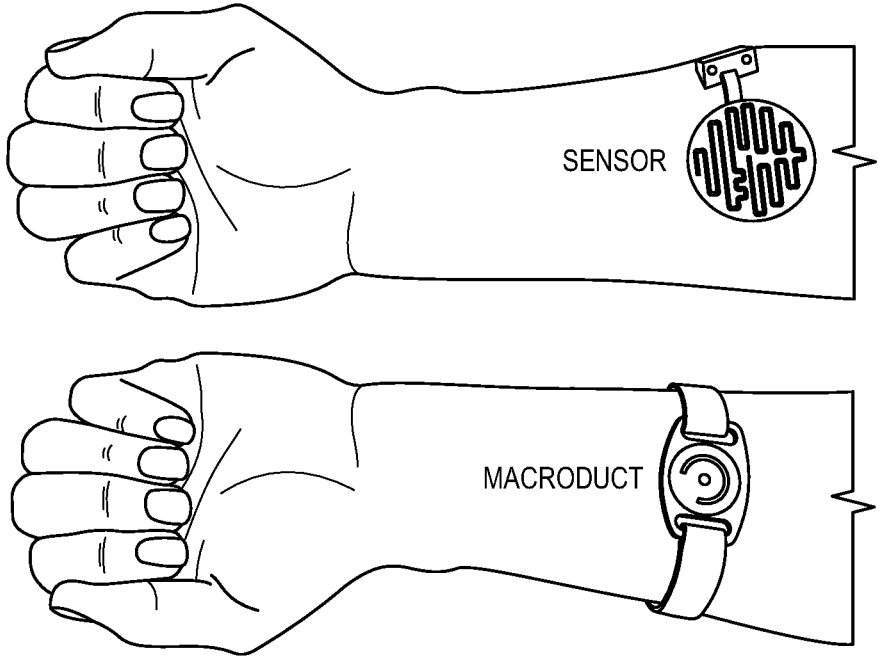
FIGS. 14A-14C illustrate the sensor output for a healthy individual measured following chemically induced sweating.
Figure 14B:
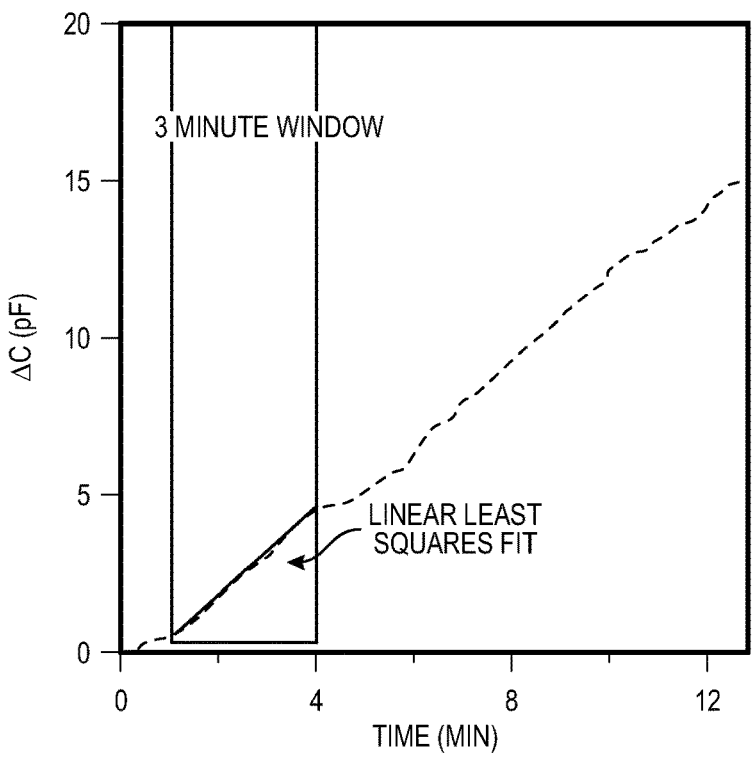
Figure 14C:
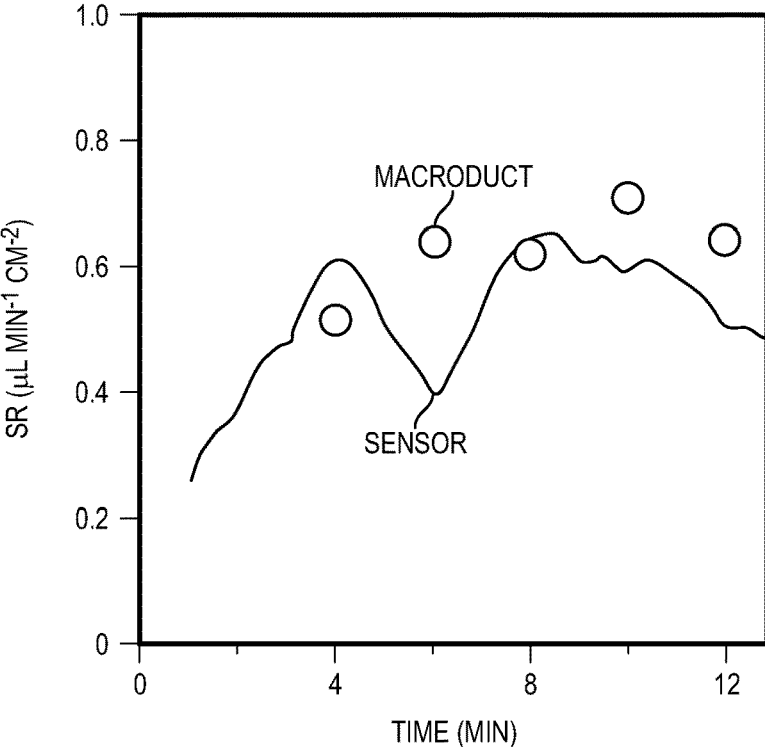

To assess the use of the sensor on the human body, trials were performed using two methods of sweat induction: (1) pilocarpine iontophoresis and (2) exercise. For chemical sweat induction, pilocarpine iontophoresis was sequentially performed on both forearms, and then a sweat rate sensor and a Macroduct device were placed on the right and left forearm over the region where the pilocarpine gel was located, respectively, as illustrated in FIG. 14A. FIG. 14B illustrates a graphical view of measured the changes in capacitance during the trial. The sweat rate was determined from the slope of the capacitance—time curve in a three-minute moving average window. FIG. 14C illustrates a graphical view of a measured sweat rate (line: sweat sensor, dots: Macroduct). The average sweat rate measured by the sensor was 0.57±0.07 (mean±S.D.) μL min⁻¹ cm⁻² from 4-12 minutes. The sweat rate determined from analysis of the Macroduct device over the same time period was 0.63±0.07 μL min⁻¹ cm⁻². These results show excellent agreement between the capacitive sensor and the value obtained from the Macroduct collection device.

Figure 14D:
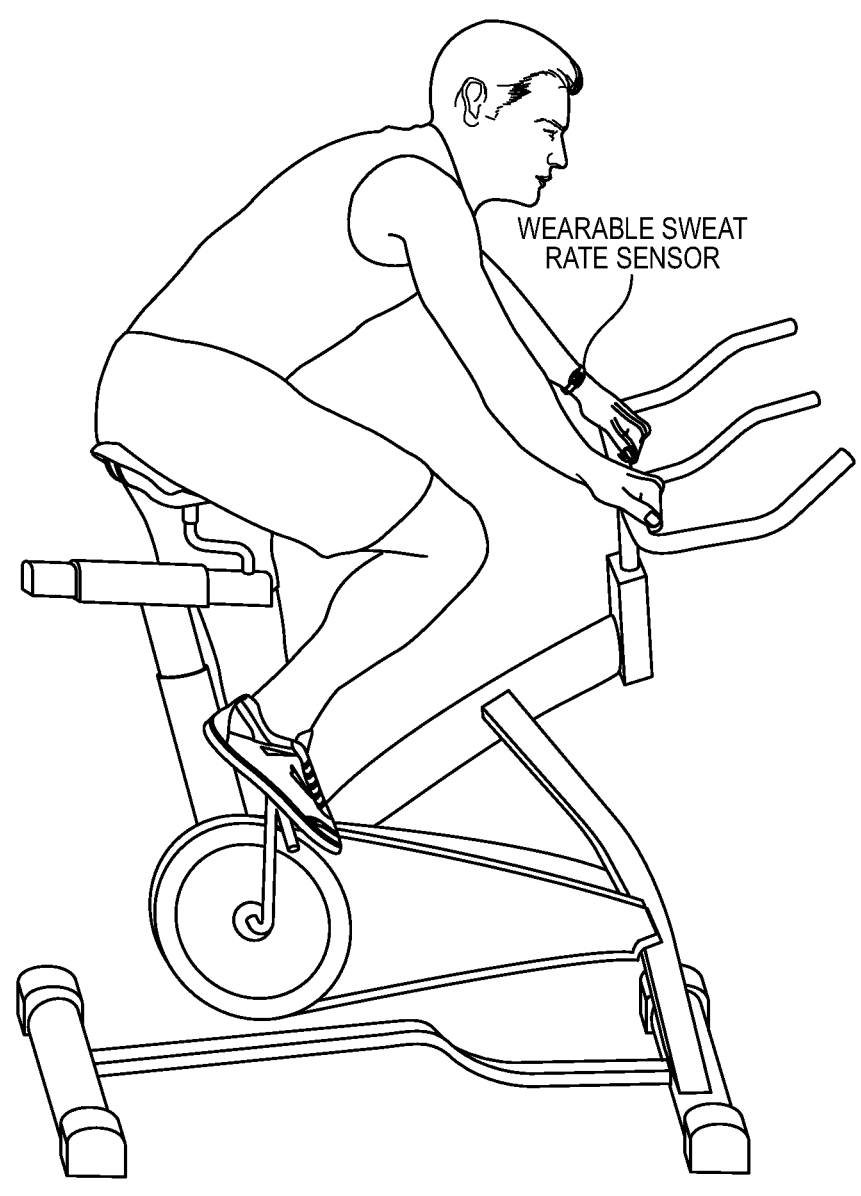
FIGS. 14D-14F illustrate the sensor output for a healthy individual measured during exercise-induced sweating.
Figure 14E:
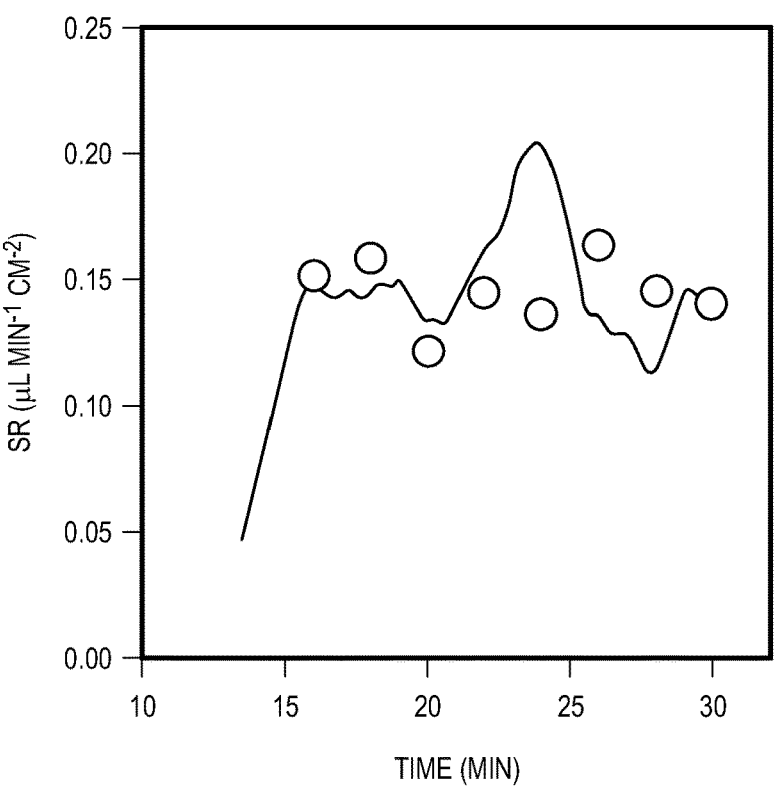
Figure 14F:
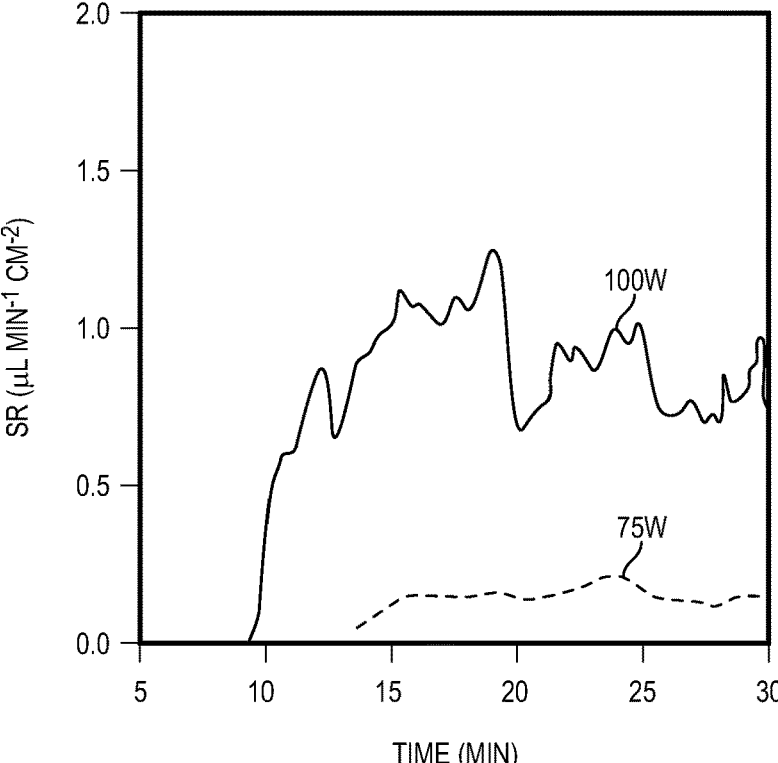

FIGS. 14D-14F illustrate the sweat rate measured during exercise-induced sweating. FIG. 14D illustrates the measurement set-up. A healthy subject was asked to spin on a stationary bike at 75 W of the exercise intensity for 30 minutes, and his sweat rate was measured using the sweat rate sensor and the Macroduct device during the trial. Average sweat rates measured by the sensor and the Macroduct device during an identical period (16 to 30 minutes) were 0.15±0.02 and 0.15±0.01 μL min⁻¹ cm⁻², respectively, as illustrated in FIG. 14D. FIG. 14E illustrates a graphical view of the measured sweat rate at 75 W exercise intensity (line: sweat sensor, dots: Macroduct). FIG. 14F illustrates a graphical view of sweat rates obtained from an identical subject at two different exercise intensities of 75 and 100 W.

To measure total electrolyte loss during exercise, simultaneous measurement of sweat rate and sweat concentration may be performed. Because sweat conductivity is directly related to sweat concentration, the sweat concentration can be obtained by measuring the sweat conductivity. To measure the sweat conductivity, two additional electrodes are integrated into the microfluidic channel of our sweat rate sensor, as described above.

Figure 15A:
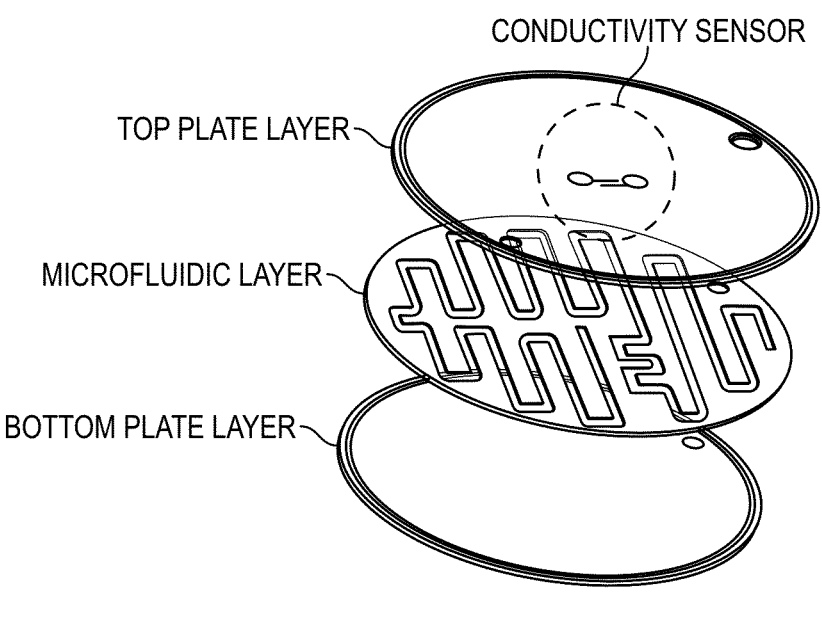
FIG. 15A illustrates a schematic diagram of an embodiment of the sensor, which can simultaneously measure sweat rate and sweat conductivity (circle: sweat conductivity sensor to measure sweat concentration).
Figure 15B:
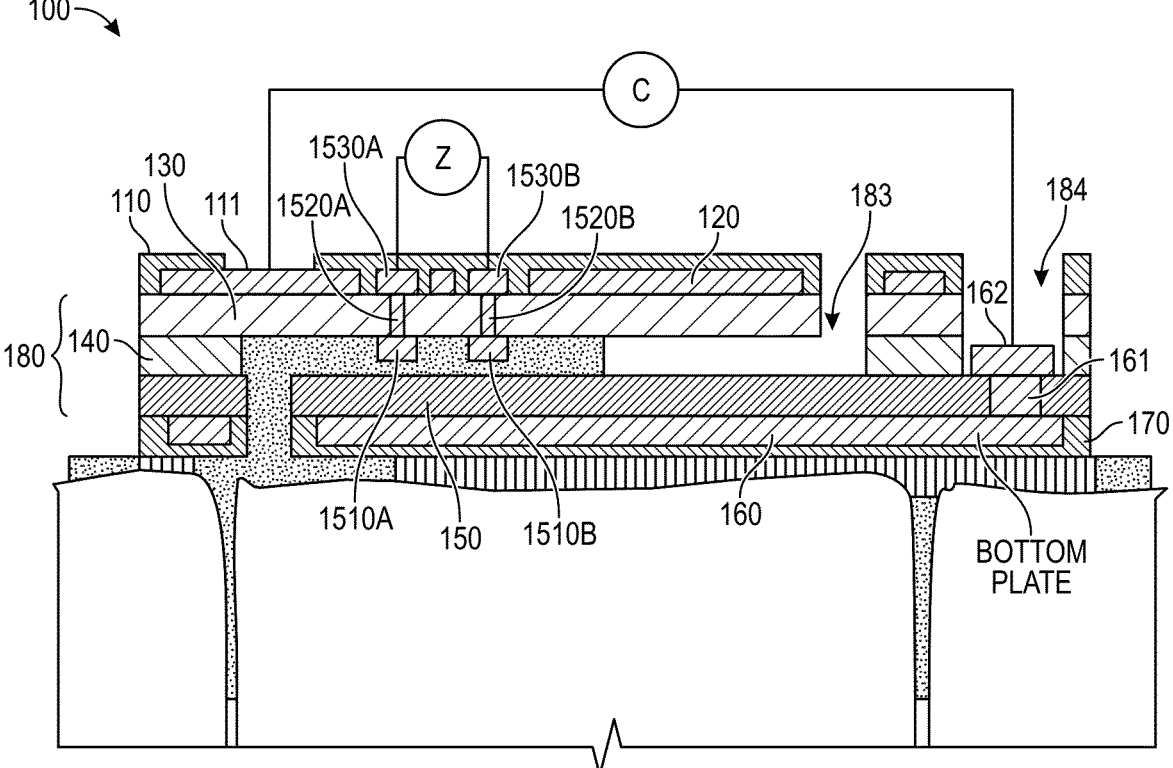
FIG. 15B illustrates a cross-sectional view of the device. The conductivity sensor is exposed to the sweat sample collected in the microfluidic channel.
Figure 15C:
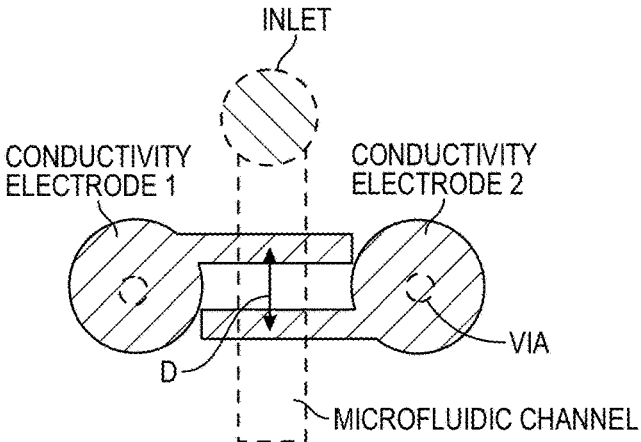
FIGS. 15C-15D illustrate the specific design of the electrodes for the conductivity sensor.
Figure 15D:
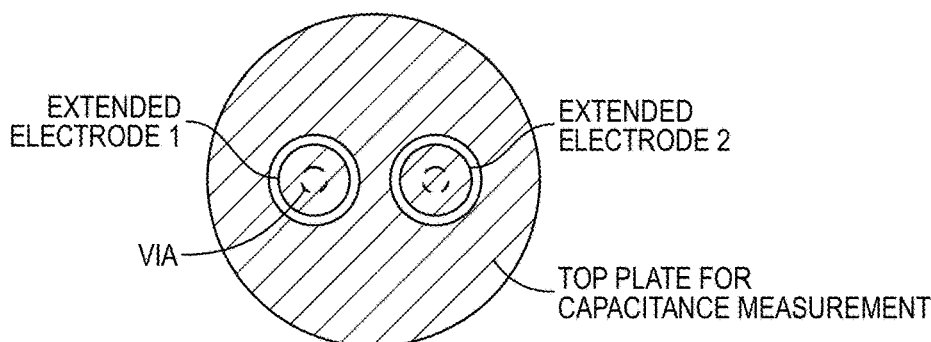
Figure 15E:
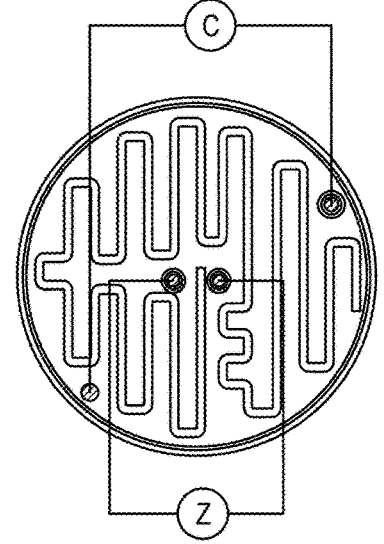
FIG. 15E illustrates the location of the electrical contacts for sweat rate and conductivity measurements.

FIG. 15A illustrates a schematic diagram of the sensor, which can simultaneously measure sweat rate and sweat conductivity (circle: sweat conductivity sensor to measure sweat concentration). FIG. 15B illustrates a cross-sectional view of the device. The conductivity sensor is exposed to the sweat sample collected in the microfluidic channel. FIGS. 15C-15D illustrates a specific design of the conductivity sensor. FIG. 15C illustrates a bottom, and FIG. 15D illustrates a top view, of the sweat conductivity sensor. To measure the concentration of the sweat sample newly collected in the microfluidic channel, the conductivity sensor may be placed near the inlet of the microfluidic channel and the distance (d) between conductivity electrodes should be short. FIG. 15E illustrates the output of the sensor.

Figure 16:
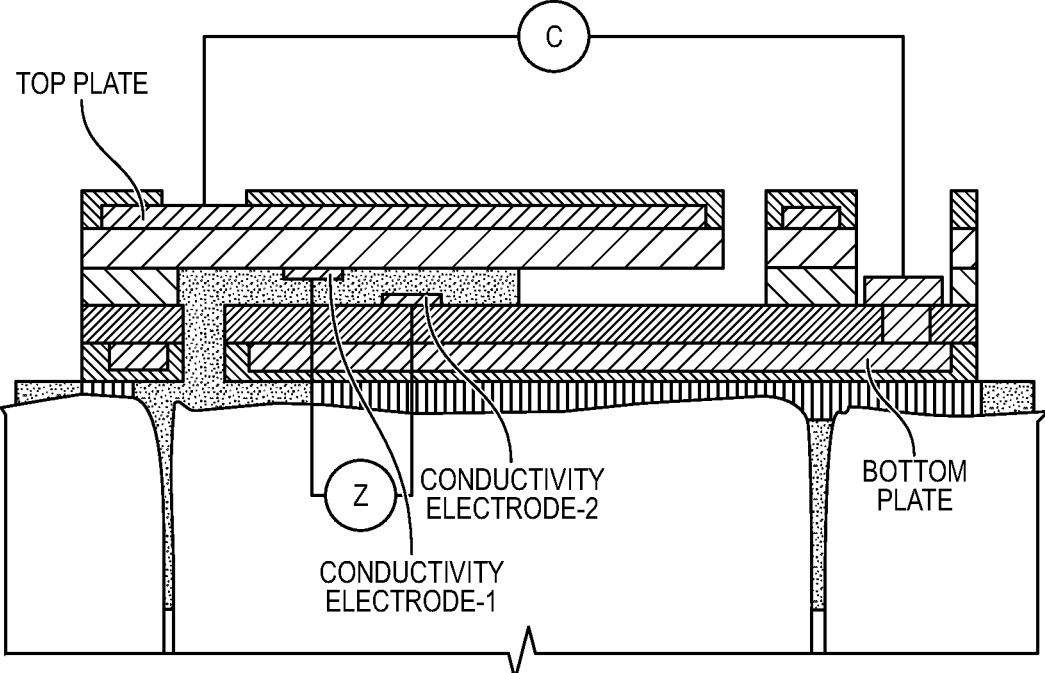
FIG. 16 illustrates an embodiment of a sweat sensing device according to the present disclosure with the conductivity electrodes facing one another.

To simultaneously measure the sweat rate and sweat concentration, a conductivity sensor may be formed on the top plate layer 120, as illustrated in FIG. 15A. The conductivity sensor may include two conductivity electrodes 1510A, 1510B, via holes 1520A, 1520B, and two extended conductivity electrodes 1530A, 1530B. The conductivity electrodes 1510A, 1510B are on opposite faces of the microfluidic channel and are exposed to the sweat sample, as illustrated in FIGS. 15B and 15C. The extended conductivity electrodes 1530A, 1530B are formed on the opposite side of the substrate 130 and electrically isolated from the top plate 120 for capacitance measurement, as illustrated in FIG. 15D. The conductivity and extended conductivity electrodes 1510A, 1530A and 1510B, 1530B are electrically connected through the vias 1520A, 1520B. The conductivity of the sweat fluid sample can be obtained by measuring the impedance (Z) between the conductivity electrodes 1510A, 1510B, as illustrated in FIGS. 15B and 15E. To measure the concentration of the sweat sample in the microfluidic channel in real time, the conductivity sensor is placed near the inlet of the fluidic channel, and the distance (d) between the conductivity measurement may be short, as illustrated in FIG. 15C. Depending on the sensor design, the conductivity electrodes 1510A, 1510B can be placed in the same plane, as illustrated in FIG. 15B or face each other as illustrated FIG. 16.

Figure 17A:
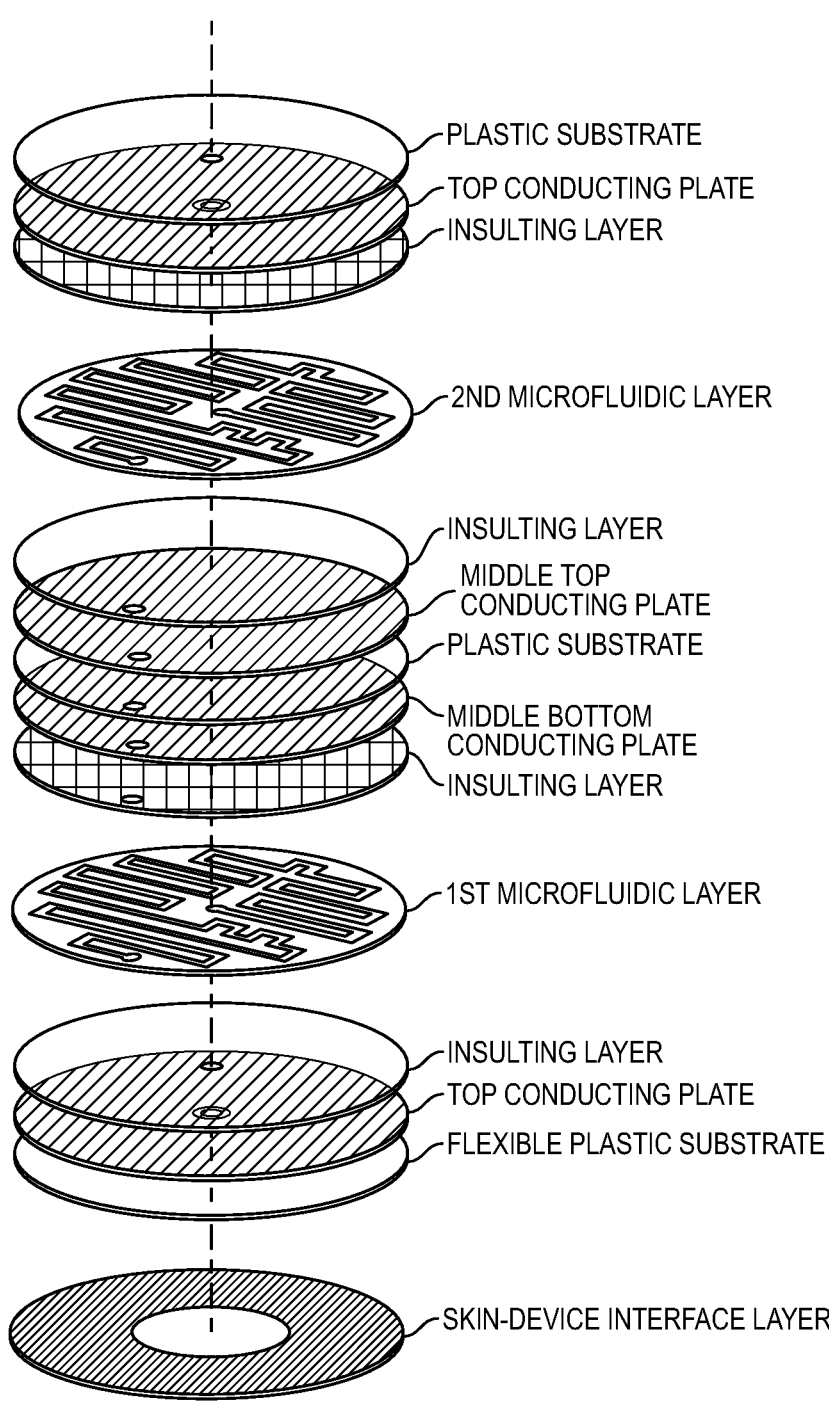
FIGS. 17A and 17B illustrate an embodiment of a sweat sensing device according to the present disclosure wherein the elements of the sensing device are stacked vertically.
Figure 17B:
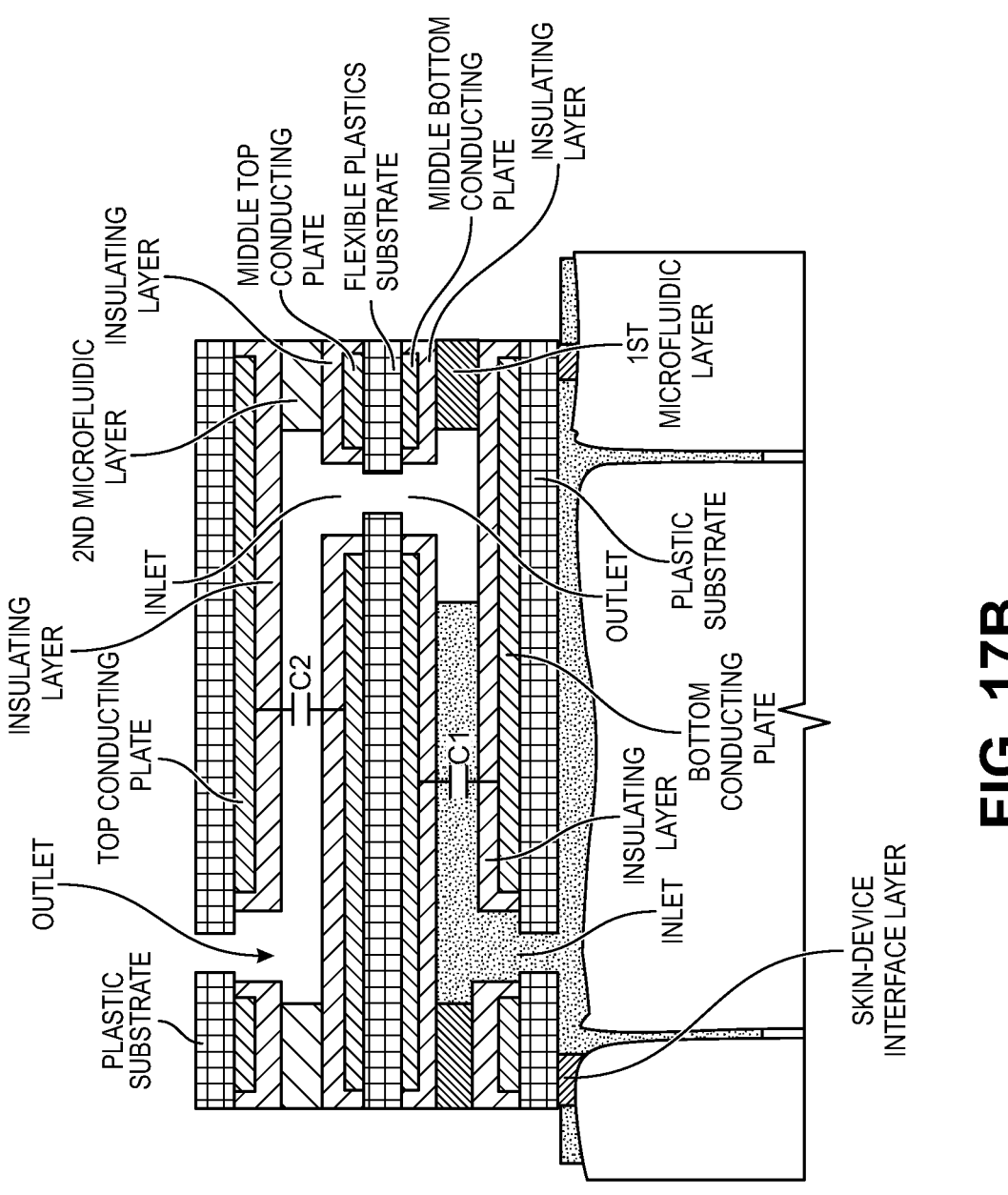

The capacity determines the usage time of a single sensor. To increase sweat capacity (e.g., the sweat volume collected in the sensor) with the same sensor footprint, the microfluidic channels can be vertically stacked, as illustrated in FIG. 17A. Depending on the design of the sensor, two or more microfluidic channels can be vertically stacked. In the embodiment of the present disclosure illustrated in FIGS. 17A-17B, the sweat rate sensor includes four (top, middle top, middle bottom, bottom) parallel conducting plates formed on a plastic substrate, two microfluidic layers, four insulating layers covering the conducting plates, and a skin-sensor interface layer. The middle top and middle bottom parallel plates are formed on opposite sides of a plastic substrate and can be connected by a via. The first microfluidic layer is formed between the middle bottom and bottom conducting plates by interposing the microfluidic layer between the two insulating layer covering the conducting plates. The second microfluidic layer is formed between the top and middle top conducting plates by interposing the microfluidic layer between the two insulating layers covering the conducing plates. The inlet and outlet of the first microfluidic layer are connected to the hole of the bottom conducting layer and the inlet of the second microfluidic layer, respectively. The inlet and outlet of the second microfluidic layer are connected to the outlet of the first microfluidic layer and the hole of the top conductive, respectively. During respiration, the sweat sequentially fills the first and second microfluidic channels. A readout circuit measures the total capacitance (parallel or series connection) of C1 and C2, where C1 is the capacitance between the bottom and middle bottom conducting plates, and C2 is the capacitance between top and middle top conducting plates of the sensor. The values of C1 and C2 values can be measured separately by a readout circuit.

The communications protocols described herein can be executed with a program(s) fixed on one or more non-transitory computer readable medium. The non-transitory computer readable medium can be loaded onto a computing device, server, imaging device processor, smartphone, tablet, phablet, or any other suitable device known to or conceivable by one of skill in the art.

Any computing necessary can be carried out using a computer, non-transitory computer readable medium, or alternately a computing device, microprocessor, or other computer type device independent of or incorporated with the present disclosure. An independent computing device can be networked together with the device either with wires or wirelessly. Indeed, any suitable method of analysis known to or conceivable by one of skill in the art could be used. It should also be noted that while specific equations are detailed herein, variations on these equations can also be derived, and this application includes any such equation known to or conceivable by one of skill in the art.

A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape.

Although the present disclosure has been described in connection with preferred embodiments thereof, it will be appreciated by those skilled in the art that additions, deletions, modifications, and substitutions not specifically described may be made without departing from the spirit and scope of the disclosure as defined in the appended claims.

The invention claimed is:

1. A sweat sensor, comprising:
a first conductor;
a second conductor, wherein the first and second conductors are metallic plates that are parallel with one another;
a supporting layer positioned between the first and second conductors, wherein the supporting layer defines a channel that is configured to receive a sample of sweat, and wherein a measure of capacitance between the first and second conductors changes based at least partially upon a volume and/or rate of the sweat in the channel;
a substrate positioned between the first and second conductors;
a first electrode positioned at least partially within the supporting layer, wherein the first electrode is electrically-connected to the second conductor, and wherein the first electrode is electrically-isolated from the first conductor;
second and third electrodes positioned at least partially within the supporting layer, wherein the second and third electrodes are positioned on a first side of the substrate; and
fourth and fifth electrodes positioned on a second, opposing side of the substrate from the second and third electrodes.

2. The sweat sensor of claim 1, further comprising:
a first insulating layer defining an inlet configured to receive the sample of sweat, wherein the inlet is in fluid communication with the channel; and
wherein the first conductor is positioned at least partially between the first insulating layer and the supporting layer.

3. The sweat sensor of claim 2, further comprising a second insulating layer defining an outlet, wherein the outlet is in fluid communication with the channel, and wherein the second conductor is positioned at least partially between the second insulating layer and the supporting layer.

4. The sweat sensor of claim 1, further comprising a circuit configured to measure the capacitance between the first and second conductors, wherein a rate of the sweat varies with the capacitance.

5. The sweat sensor of claim 1, the second and third electrodes are positioned on opposite sides of the channel from one another and configured to be contacted by the sweat in the channel.

6. The sweat sensor of claim 5, further comprising a circuit that is configured to measure an impedance between the second and third electrodes, wherein a conductivity of the sweat varies with the impedance.

7. The sweat sensor of claim 1, wherein the sweat sensor is configured to simultaneously determine a rate of the sweat and a conductivity of the sweat.

8. A sweat sensor, comprising
a bottom insulating layer defining an inlet that is configured to receive sweat;
a bottom plate positioned above the bottom insulating layer;

a supporting layer positioned above the bottom plate, wherein the supporting layer defines a channel that is in fluid communication with the inlet;

a top substrate positioned above the supporting layer;

a top plate positioned above the top substrate, wherein the bottom plate and the top plate comprise a conductive material, and wherein the bottom plate and the top plate are parallel with one another;

a top insulating layer defining an outlet that is in fluid communication with the channel, wherein the bottom insulating layer and the top insulating layer comprise a non-conductive material;

a first electrode positioned at least partially within the supporting layer, wherein the first electrode is electrically-connected to the bottom plate, and wherein the first electrode is electrically-isolated from the top plate;

second and third electrodes positioned at least partially within the supporting layer, wherein the second and third electrodes are positioned on a first side of the top substrate;

fourth and fifth electrodes positioned on a second, opposing side of the top substrate from the second and third electrodes; and a circuit configured to:

measure a capacitance between the bottom plate and the top plate using the first electrode; and determine a rate of the sweat based at least partially upon the capacitance.

9. The sweat sensor of claim 8, further comprising:

a bottom substrate, wherein the bottom plate is coupled to the bottom substrate, and wherein the bottom substrate is positioned between the bottom plate and the supporting layer; and the top substrate, wherein the top plate is coupled to the top substrate, and wherein the top substrate is positioned between the top plate and the supporting layer.

10. The sweat sensor of claim 8, wherein the first electrode is configured to be contacted by the sweat in the channel.

11. The sweat sensor of claim 8, wherein the second and third electrodes are positioned on opposite sides of the channel and configured to be contacted by the sweat in the channel.

12. The sweat sensor of claim 11, wherein the circuit is further configured to:

measure an impedance between the second and third electrodes; and determine a conductivity of the sweat based at least partially upon the impedance.

13. A sweat sensor, comprising a bottom insulating layer configured to be placed in contact with a user's skin, wherein the bottom insulating layer defines an inlet that is configured to receive sweat from the user's skin;

a bottom plate positioned above the bottom insulating layer;

a supporting layer positioned above the bottom plate, wherein the supporting layer defines a channel that is configured to receive the sweat from the inlet;

a top substrate positioned above the supporting layer;

a top plate positioned above the top substrate, wherein the bottom plate and the top plate comprise a conductive material, and wherein the bottom plate and the top plate are parallel with one another;

a top insulating layer defining an outlet that is configured to receive the sweat from the channel, wherein the bottom insulating layer and the top insulating layer comprise a non-conductive material;

a first electrode positioned at least partially within the supporting layer, wherein the first electrode is electrically-connected to one of the bottom plate and the top plate, and wherein the first electrode is electrically-isolated from the other of the bottom plate and the top plate;

second and third electrodes positioned at least partially within the supporting layer, wherein the second and third electrodes are positioned on opposite sides of the channel and configured to be contacted by the sweat in the channel;

fourth and fifth electrodes positioned on an opposite side of the top substrate from the second and third electrodes; and a circuit configured to:

measure a capacitance between the bottom plate and the top plate using the first electrode;

determine a rate of the sweat based at least partially upon the capacitance;

measure an impedance between the second and third electrodes; and determine a conductivity of the sweat based at least partially upon the impedance.

14. The sweat sensor of claim 13, further comprising:

a bottom substrate, wherein the bottom plate is coupled to the bottom substrate, and wherein the bottom substrate is positioned between the bottom plate and the supporting layer; and the top substrate, wherein the top plate is coupled to the top substrate, and wherein the top substrate is positioned between the top plate and the supporting layer.

15. The sweat sensor of claim 13, wherein the first electrode is isolated from the channel.

16. The sweat sensor of claim 13, wherein the capacitance changes based at least partially upon a volume of the sweat in the channel.

17. The sweat sensor of claim 13, wherein a first via extends through the top substrate and electrically connects the second and fourth electrodes.

18. The sweat sensor of claim 17, wherein a second via extends through the substrate and electrically connects the third and fifth electrodes.

19. The sweat sensor of claim 18, wherein the fourth and fifth electrodes are in contact with the substrate and the top insulating layer.

20. The sweat sensor of claim 19, wherein the fourth and fifth electrodes are electrically isolated from the top plate.

* * * * *